United States Patent
Hoff et al.

(10) Patent No.: US 10,196,654 B2
(45) Date of Patent: Feb. 5, 2019

(54) METHOD FOR CYCLING BIOMASSES BETWEEN MUSHROOM CULTIVATION AND ANAEROBIC BIOGAS FERMENTATION, AND FOR SEPARATING AND DRYING A DEGASSED BIOMASS

(71) Applicant: Advanced Substrate Technologies A/S, Tjele (DK)

(72) Inventors: Svend Kristian Hoff, Odder (DK); Lars Jørgen Pedersen, Hadsten (DK)

(73) Assignee: ADVANCED SUBSTRATE TECHNOLOGIES A/S, Tjele (DK)

( * ) Notice: Subject to any disclaimer, the term of this patent is extended or adjusted under 35 U.S.C. 154(b) by 0 days.

(21) Appl. No.: 14/904,142

(22) PCT Filed: Jul. 11, 2014

(86) PCT No.: PCT/DK2014/050220
§ 371 (c)(1),
(2) Date: Jan. 11, 2016

(87) PCT Pub. No.: WO2015/007290
PCT Pub. Date: Jan. 22, 2015

(65) Prior Publication Data
US 2016/0160239 A1    Jun. 9, 2016

(30) Foreign Application Priority Data

Jul. 16, 2013   (DK) .................... 2013 00430

(51) Int. Cl.
| | |
|---|---|
| *C12P 5/02* | (2006.01) |
| *C12P 1/02* | (2006.01) |
| *C12M 1/107* | (2006.01) |
| *C12M 1/00* | (2006.01) |
| *C12N 1/14* | (2006.01) |
| *C12M 1/12* | (2006.01) |

(52) U.S. Cl.
CPC ............ *C12P 5/023* (2013.01); *C12M 21/04* (2013.01); *C12M 25/00* (2013.01); *C12M 47/10* (2013.01); *C12M 47/14* (2013.01); *C12M 47/16* (2013.01); *C12N 1/14* (2013.01); *C12P 1/02* (2013.01); *Y02E 50/343* (2013.01); *Y02P 20/582* (2015.11)

(58) Field of Classification Search
None
See application file for complete search history.

(56) References Cited

U.S. PATENT DOCUMENTS

| | | |
|---|---|---|
| 5,557,873 A | 9/1996 | Lynam |
| 7,883,884 B2 | 2/2011 | Bonde et al. |
| 2002/0164730 A1 | 11/2002 | Ballesteros Perdices et al. |
| 2004/0025715 A1 | 2/2004 | Bonde et al. |
| 2011/0091954 A1* | 4/2011 | Chen ............... A01H 13/00 435/168 |

FOREIGN PATENT DOCUMENTS

| | | |
|---|---|---|
| CN | 101496485 | 8/2009 |
| CN | 103172450 | 6/2013 |
| EP | 1688475 | 9/2006 |
| EP | 1911848 | 4/2008 |
| GB | 2161466 | 1/1986 |
| WO | WO-2006/110901 | 2/2006 |
| WO | WO-2006/110891 | 10/2006 |
| WO | WO-2015/007290 | 1/2015 |
| WO | WO-2016/116113 | 7/2016 |

OTHER PUBLICATIONS

Muller, H.W. et al. 1986. Screening of white-rot fungi for biological treatment of wheat straw for biogas production. Applied Microbiology and Biotechnology 24: 180-185. specif. pp. 180, 184.*
Sanchez, C. 2009. Lignocellulosic residues: biodegradation and bioconversion by fungi. Biotechnology Advances 27: 185-194. specif. pp. 185, 186, 191, 192.*
Arsova, L. 2010 May.Anaerobic digestion of food waste. Datasheet [online]. Dept. of Earth and Environmental Engineering, Columbia University. [retrieved on May 4, 2017]. Retrieved from the Internet: <URL: http://www.seas.columbia.edu/earth/wtert/sofos/arsova_thesis.pdf> pp. 1-77. specif. pp. 8, 13, 51, 55, 63.*
Kazakevich, V. et al., Ammonia Treat Straw Animal Feed Manufacture Chamber Load Unload Press Conveyor Steam Heat Supply System, Feb. 23, 1991 (WPI Thomson Abstract only).
Bisaria, R. et al., Utilization of spent agro-residues from mushroom cultivation for biogas production, *Applied Microbiology and Biotechnology*, 33: 607-9, 1990.
Li, C. et al., A kinetic study on enzymatic hydrolysis of a variety of pulps for its enhancement with continuous ultrasonic irradiation, *Biochemical Engineering Journal*, 19: 155-164, 2004.
Lopez, M. et al., Biodelignification of agricultural and forest wastes: Effect on anaerobic digestion, *Biomass and Bioenergy*, 58:343-349, 2013.
Mosier, N. et al., Features of promising technologies for pretreatment of lignocellulosic biomass, *Bioresource Technology*, 96: 673-686, 2005.
Schell, D. et al., Dilute-Sulfuric Acid Pretreatment of Corn Stover in Pilot-Scale Reactor, *Applied Biochemistry and Biotechnology*, 105-108: 69-85, 2003.
Zhu, S. et al., Production of ethanol from microwave-assisted alkali pre-treated wheat straw, *Process Biochemistry*, 41: 869-873, 2006.
Database WPI (Grass straw process), Kazakevich 1991.

* cited by examiner

*Primary Examiner* — Renee Claytor
*Assistant Examiner* — Sharon M. Papciak
(74) *Attorney, Agent, or Firm* — Dinsmore & Shohl LLP

(57) ABSTRACT

The present invention is related to recycling of fermentable and metabolizable biomass materials for sequentially performing a cultivation of fungal cells and for producing biogas by anaerobic fermentation of said biomass materials.

22 Claims, 8 Drawing Sheets

METHOD FOR CYCLING BIOMASSES BETWEEN MUSHROOM CULTIVATION AND ANAEROBIC BIOGAS FERMENTATION, AND FOR SEPARATING AND DRYING A DEGASSED BIOMASS

FIELD OF INVENTION

The present invention relates to biomass material processing and renewable energy production. In particular, the invention relates to a method for anaerobic fermentation of a biomass material, production of biogas, and separating and drying the spent biomass material to produce a fibrous solid fraction capable of being used as a substrate for cultivating fungal cells. Also disclosed are combined methods for producing biogas and obtaining from the degassed biomass a fibrous solid fraction and using said fibrous solid fraction as a substrate for cultivating fungal cells. Recycling of the thus produced spent fungal substrate back to a biogas fermenter and supplementing the spent fungal substrate with e.g. organic waste biomasses are also disclosed.

BACKGROUND OF INVENTION

Many traditional energy sources, such as e.g. fossil fuels, are being depleted faster than new ones are being made. Fossil fuels are non-renewable resources because they take millions of years to form. Also, use of fossil fuels raises serious environmental concerns. Renewable energy sources represent a promising alternative to many traditional energy sources. Biomass represents one source of renewable energy.

If biomass energy is to have a long-term, commercial future, the organic material must be processed to generate affordable, clean and efficient energy forms, such as liquid and gaseous fuels, or electricity. Biomass processing is important to ensure an efficient exploitation of the biomass energy. However, the energy potential can often be difficult to exploit. An increased exploitation of the energy potential of a biomass may result in an increased production of renewable energy sources, such as biogas.

Additionally, spent biomass materials having a reduced organic nitrogen content can be upgraded, sanitized and re-used in the production of many edible products.

Extensive scientific and engineering work has been conducted on the biogasification of waste materials. The fundamental technique relies on an anaerobic digestion or fermentation process. However, anaerobic microorganisms responsible for methanogenesis are inhibited by ammonia and methanogenesic anaerobic bacteria are inhibited by and cease to metabolise nutrients effectively at high ammonia concentration levels.

The problems associated with ammonia inhibition have made currently available technical solutions difficult to operate—especially when using biomasses containing relatively high amounts of nitrogen.

To mitigate these problems, it has been attempted to control the carbon to nitrogen (C/N) ratio of the biomass material subjected to fermentation. However, state-of-the-art solutions continue to suffer from a number of disadvantages. For example, adjusting the ammonia concentration in a reactor by adjusting the C/N ratio of the biomass is a slow process, and adjusting the C/N ratio may prove insufficient when handling biomasses prone to generating relatively high ammonia concentrations during anaerobic digestion.

Lime pressure cooking and ammonia stripping has been disclosed as a way to reduce the amount of organic and inorganic nitrogen present in a biomass to be subjected to anaerobic fermentation. Reference is made e.g. to U.S. Pat. No. 7,883,884.

Furthermore, many complex biomasses contain macromolecular constituents which are difficult to metabolize for microbial organisms traditionally involved in the production of biogas. In particular, macromolecular constituents, such as cellulose, hemicellulose, lignocellulose and lignin, are present in many biomass materials and can only be metabolized to a limited extent during a biogas fermentation process.

There is a need for improved and more cost effective pre-treatment methods for rendering the afore-mentioned, recalcitrant biomass material constituents more accessible for many microbial organisms present during different stages of a biogas production.

SUMMARY OF INVENTION

The present invention generally relates to a combined method for manufacturing and recycling a fibrous solid fraction obtained from an anaerobic biogas fermentation for cultivating *Basidiomycete* cells, and subsequently using the spent *Basidiomycete* substrate as a feed stock biomass material in the anaerobic biogas fermentation from which the fibrous solid fraction used for the cultivation of the basiciomycete cells was obtained.

In one aspect of the present invention there is provided a method for manufacturing a fibrous solid substrate suitable for cultivating *Basidiomycete* cells.

In another aspect of the present invention there is provided a method for cultivating fungal cells, including *Basidiomycete* cells, and/or spores, on a fibrous solid substrate.

In yet another aspect of the present invention there is provided a method for recycling biomass materials comprising organic and inorganic nitrogen parts selected from spent, fungal species substrate biomass materials and degassed, fermented biomass materials.

In a still further aspect of the present invention there is provided a method for controlling the composition of nutrients of a fibrous solid substrate suitable for cultivating *Basidiomycete* cells.

In a still further aspect of the present invention there is provided a method for controlling the moisture content and the composition of nutrients of a fibrous solid fraction comprising organic and inorganic nitrogen parts suitable for cultivating *Basidiomycete* cells.

In a yet further aspect of the present invention there is provided a method for separating and drying a biomass material comprising organic and inorganic nitrogen parts, and providing a fibrous solid substrate suitable for cultivating *Basidiomycete* cells.

In a still further aspect of the present invention there is provided a method for reducing the content of inorganic nitrogen compounds in a fibrous solid fraction comprising organic and inorganic nitrogen parts of a biomass material comprising organic and inorganic nitrogen parts and providing a fibrous solid substrate suitable for cultivating *Basidiomycete* cells.

In a still further aspect of the present invention there is provided a method for increasing the relative amount of organic nitrogen content of a fibrous solid fraction comprising organic and inorganic nitrogen parts of a biomaterial following fermentation and biogas production.

In yet another aspect of the present invention there is provided a method for fractionating a biomass material and obtaining a) a fibrous solid fraction comprising solid and liquid parts, said fibrous solid fraction further comprising organic and inorganic nitrogen parts, b) at least one liquid fraction comprising solid and liquid parts, and c) a phosphor-containing fraction or sediment.

In a still further aspect of the present invention there is provided a method for producing a biogas by anaerobic fermentation of a biomass material.

In a yet further aspect of the present invention there is provided a method for producing biogas and gasses comprising volatile nitrogen containing compounds by sequential, anaerobic fermentations and stripping at least partly said volatile nitrogen containing compounds, including ammonia, from the fermented biomass materials comprising organic and inorganic parts.

In a still further aspect of the present invention there is provided a method for producing biogas and reducing or eliminating the emission from a biogas fermentation facility of undesirable odorants in the form of gasses comprising volatile nitrogen containing compounds, and optionally also sulphur containing compounds, by sequential, anaerobic fermentations and stripping at least partly said volatile nitrogen containing compounds, and optionally also said volatile sulphur containing compounds, including ammonia and, when present, hydrogen sulphide, from the fermented biomass materials comprising organic and inorganic parts.

In yet another aspect of the present invention there is provided a method for sequential fermentation of a biomass material.

In a yet further aspect of the present invention there is provided a method for obtaining a feed stock biomass material suitable for use in an anaerobic biogas fermentation.

In a still further aspect of the present invention there is provided a method for sequentially and differentially fermenting a biomass material comprising different bioenergy sources.

In yet another aspect of the present invention there is provided a method for producing and collecting first and second volatile compounds through sequential fermentations of a fermentable biomass material.

Definitions

Batch fermentation: Unit operation of a fermenter where one fermenter cycle of e.g. feedstock preparation, biogas fermentation, volatile compound production, and product formation is completed before the next fermentation cycle is started.

Bioenergy: The production, conversion, and use of material directly or indirectly produced by photosynthesis (including organic waste) to manufacture fuels and substitutes for petrochemical and other energy-intensive products.

Biogas: a mixture of gases produced by the breakdown of organic matter in the absence of oxygen. Biogas primarily contain methane ($CH_4$), and also carbon dioxide ($CO_2$), and may have small amounts of hydrogen sulphide ($H_2S$), moisture and siloxanes.

Biomass material: Organic material comprising fermentable carbon and nitrogen sources capable of being utilized by microbial organisms in a fermentation.

Continuous fermentation: A steady-state fermentation system in which substrate is continuously added to a fermenter while products and residues are removed at a steady rate.

Cooking: A process to turn dry starch and water into liquefied mash (water, grain hulls+germ, & dextrins) using pH controls, set temperature parameters, solids controls, & enzymes.

Dewatering: The separation of free water from the solids portion of e.g. fibrous solid fractions, spent mash, sludge, or whole stillage by screening, centrifuging, filter pressing, or other means.

Digestate: Solid fraction obtained from anaerobic fermentation and biogas production. A digestate comprises a fibrous fraction, non-fibrous solids, such as minerals, and a liquid fraction. Anaerobic digestion produces two main products: digestate and biogas.

Feedstock biomass material: A substance used as a raw material in a fermentation.

Fermentation: Biological conversion of biomass materials. Fermentation is one of several steps in the processing of biomass. A fermentation is collectively all of the metabolic processes involved in the conversion of fermentable sugars into one or more fermentation end products, such as e.g. gases, acids and alcohols.

Fiber/fibrous material: Residual fraction of plant origin and part of a digestate resulting from an anaerobic fermentation and biogas production. The chemical composition of a fibrous material or fraction can comprise or consist of e.g. cellulose and hemi-cellulose, lignin, lignocellulose, and additional plant components, such as e.g. dextrins, inulin, chitins, pectins, and beta-glucans N-mineralization: Process of converting ammonium (ions) into ammonia (gas).

N-stripping: Process of removing volatile nitrogen containing compounds by evaporation.

N-water: Residual liquid fraction comprising small amounts of largely inorganic nitrogen containing compounds.

$NH_3$: Gaseous ammonia—inhibitory for a biogas fermentation in high concentrations. An example of a volatile nitrogen-containing compound.

$NH_4+$: Ammonium ion or ammonium salt. Capable of being converted into gaseous ammonia. An example of a precursor compound of a volatile nitrogen-containing compound.

Permeate: Liquid fraction resulting from a separation process in which a biomass material is separated into a fibrous solid fraction and one or more liquid fractions comprising solid and liquid matter. The permeate is an essentially liquid fraction void of solid substances.

Pre-digested biomass material: Feed stock biomass material for an anaerobic fermentation obtained from a prior performed anaerobic fermentation.

Slurry: Manure with a total solids concentration of between approximately 5 and 15 percent. Slurries are pumpable. Above a total solids concentration of 15 percent, slurries are semisolids with a negligible angle of repose and can be scraped but not stacked for storage.

Stripping-off volatile compounds: Process of performing an evaporation under conditions at which volatile compounds will be present on a gaseous form.

While conventional biogas reactors can be operated using e.g. manures, organic waste materials, corn silage, whey and dairy waste, sludge from cheese production, as well as vegetable oils, biogas reactors operated in accordance with the present invention can be operated using a wide range of organic materials having a high content of nitrogen such as complex wastes, especially when employing a first fermentation step in a pre-fermentation facility unit (indicated as a pre-reactor), where the primary aim is removal of first volatile solid such as nitrogen rather than biogas production.

Figure 1:
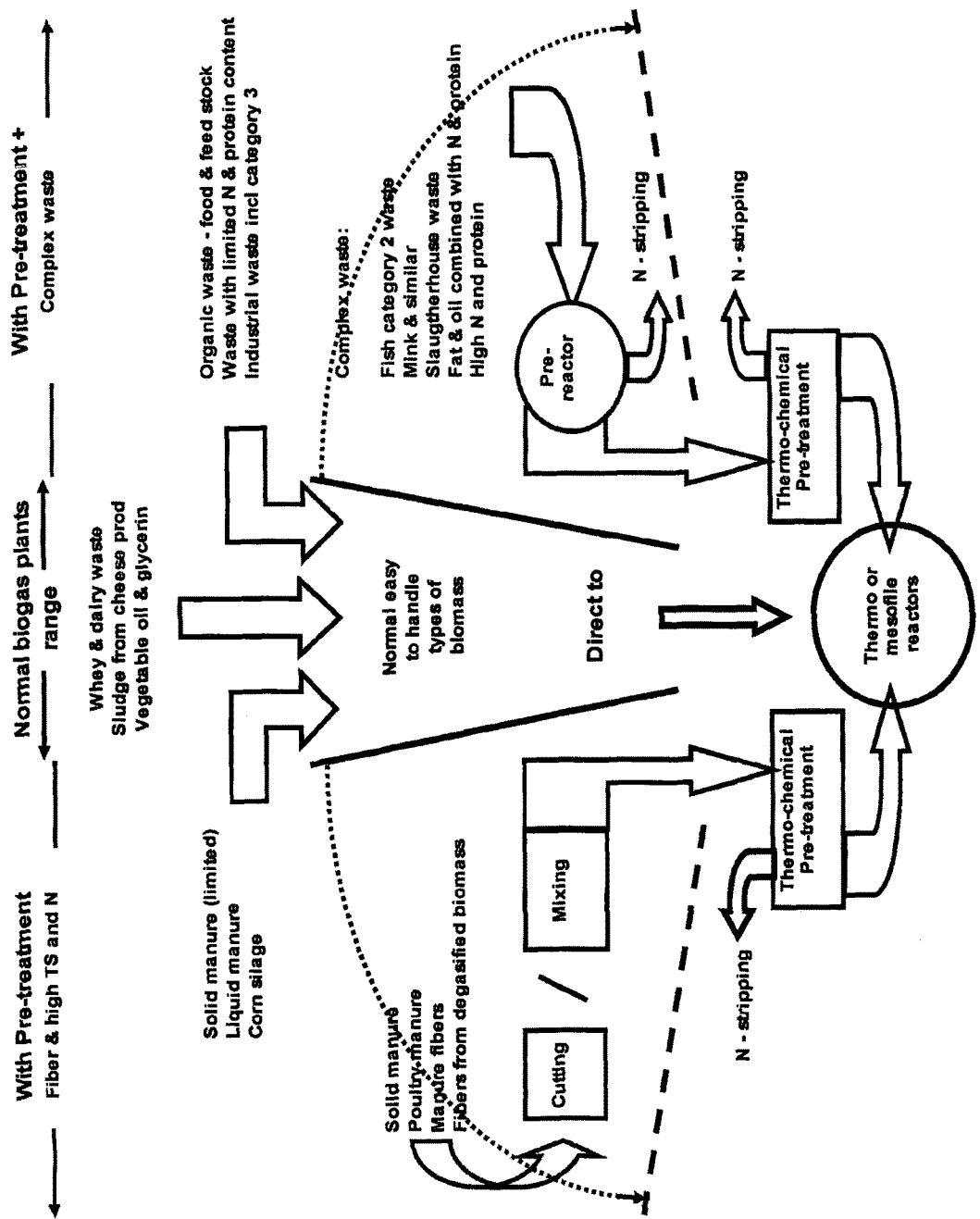
FIG. 1 illustrates the principle of producing biogas comprising operating one or more biogas reactors and one or more fermentation(s) of different biomasses; directly in a fermentation facility (thermo or mesophile reactors) for normal and easy to handle waste, and in one embodiment following a pre-treatment based on the type and complexity of biomass such as a thermo-chemical pre-treatment, such as e.g. lime pressure cooking resulting in stripping of ammonia N.
Figure 2:
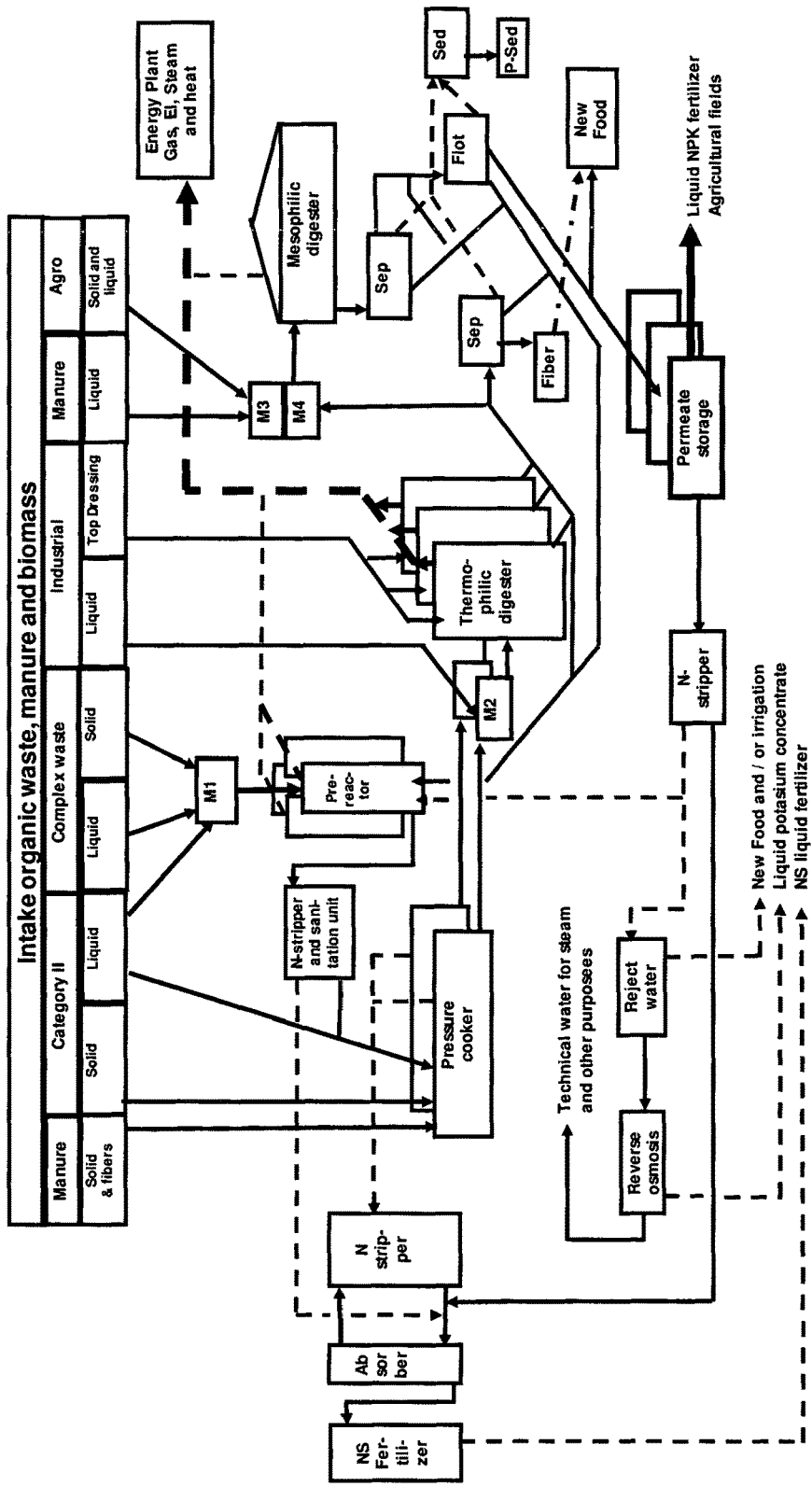

FIG. 2 illustrates a process flow for various biomass types in accordance with an embodiment of the present invention. Simpler manure and agro waste is directly treated in the fermentation facility (mesophilic digester) after mixing in M3 and M4. Industrial waste material is sent to the mesophilic digester after having undergone a thermophilic digestion step.

The waste may first undergo a mixing step in mixer M2. For manure and/or some category II waste, a thermo-chemical treatment in the pressure unit (pressure cooker) is employed prior to sending the waste to the fermentation facility. The pressure cooker is operationally connected with N-stripper for stripping the nitrogen produced during the hyrolysis process in the pressure unit.

For complex waste and some category II waste, a further pre-treatment step in the pre-reactor is performed prior to the thermo-chemical treatment, to maximize the conversion of organic N and protein. The pre-reactor is operationally connected with an N-stripper and sanitation unit, for passing before sending the sanitized first fermented biomass for the thermo-chemical treatment in the pre-reactor, followed by the fermentation for production of biogas. As part of post-processing, separation techniques may be employed for obtaining valuable recoverable like N, P, K, water.

Figure 3:
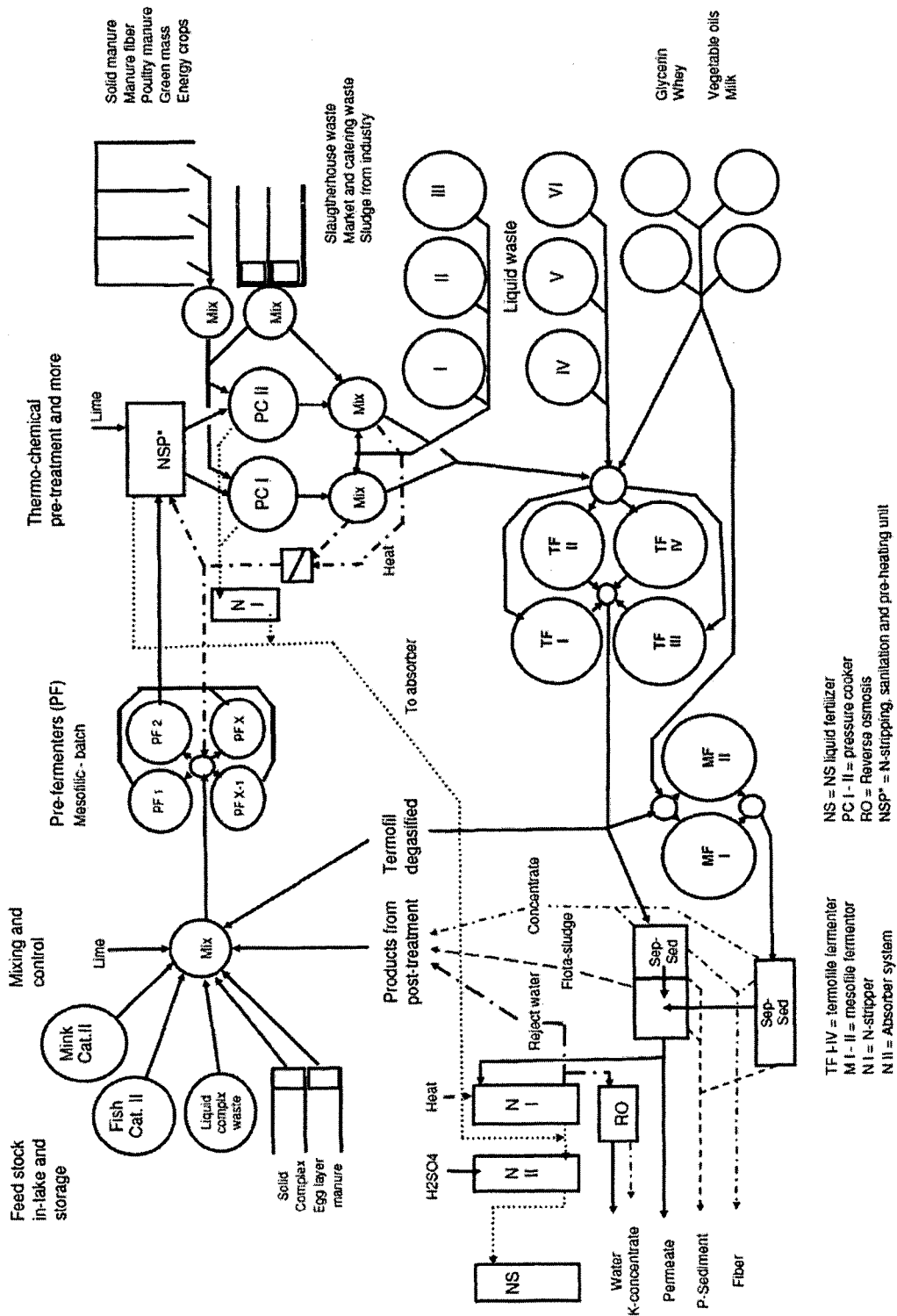

FIG. 3 illustrates a system diagram for employing the process in accordance with an embodiment of the invention. In particular, the system includes feed stock in-take and storage that provides category II and/or complex biomass for biogas generation utilizing the first fermentation facility unit (pre-fermentors) and N-stripper and sanitation unit. The stripper and sanitation unit being connected to pressure unit (pressure cooker) where hydrolyses takes place. The pressure units are in-turn connected to the fermentation facility that may include a plurality of either thermophilic digesters or mesophilic potentially being interconnected.

In other embodiments, there are biomass feed facility directly to the pressure unit (see Liquid waste I, II, and II), the biomass fed directly is then sent to the fermentation facility after hydrolysis in the pressure unit. In another embodiment, the biomass may also be directly fed to the fermentation facility—either directly to the thermophilic fermentors or directly to the mesophilic fermentors or in sequence, as shown by liquid waste IV, V and VI or by feed input of glycerin, vegetable oil, milk and whey. In another embodiment, the pre-fermentors of the pre-fermentation facility are directly connected to the fermentation facility fermentors as well. In yet another embodiment there is provided a closed loop between the pressure unit and the pre-fermenters for allowing further fermentation of the biomass material.

Figure 4:
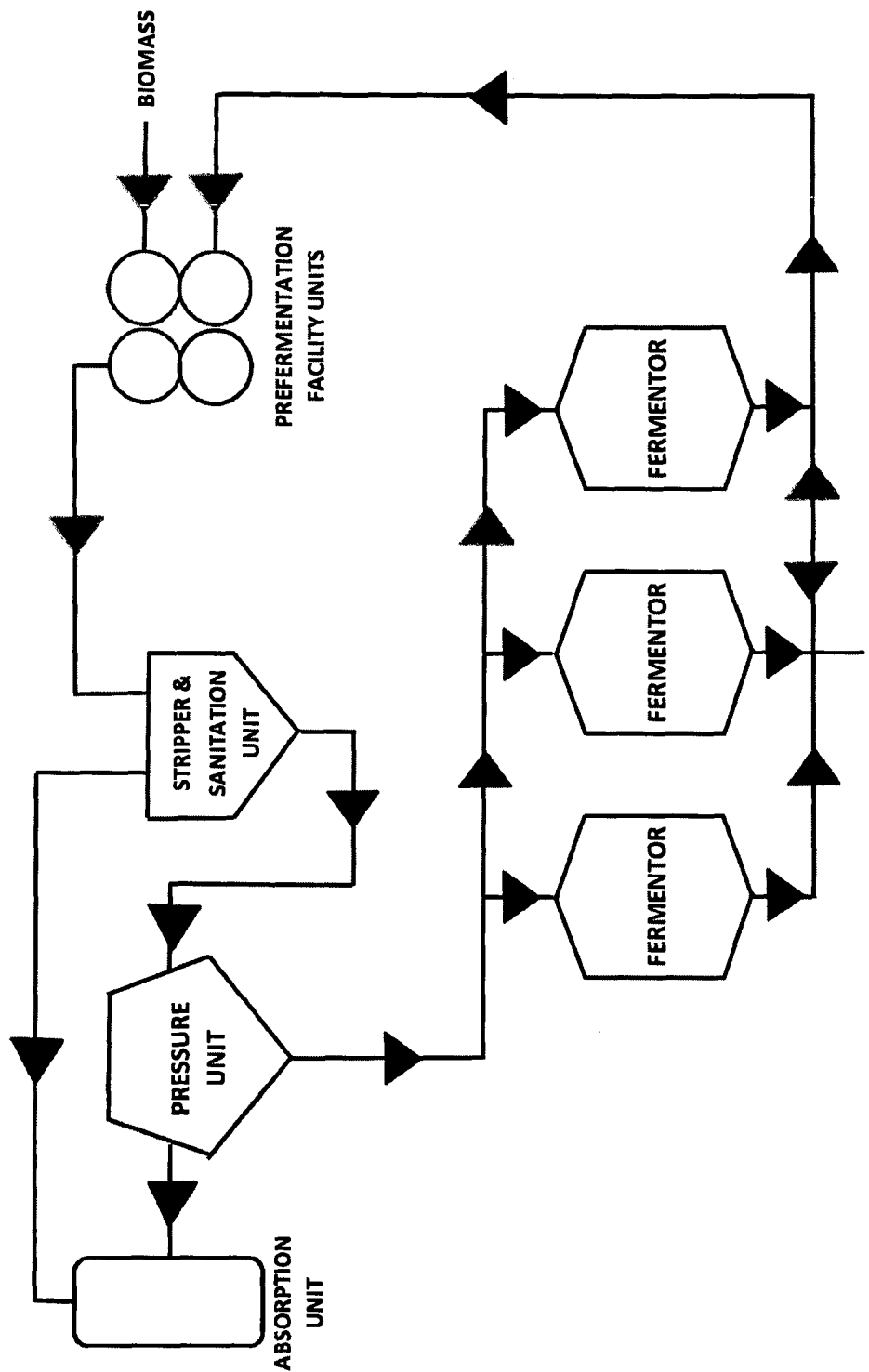

FIG. 4 illustrates a block diagram of system for handling complex waste according to an embodiment of the invention. The biomass is first fermented in the pre-reactor facility, thereafter the first fermented biomass is diverted to the stripper and sanitation unit. The ammonia generated during the first fermentation is stripped off and absorbed. The sanitized first fermented biomass is subjected to pressure cooking (with or without addition of lime) in the pressure unit and the ammonia generated during this stage is stripped off and absorbed. The hydrolyzed biomass with reduced N content is then diverted to the fermenters for anaerobic fermentation and production of biogas. Some amount of the biomass that gets fermented in the fermenters may be diverted back to the pre-fermenters, where the amount acts as a starter culture for facilitating initiation of fermentation in the pre-fermenters. In some situations, the first fermented biomass may skip the thermo-chemical treatment in the pressure unit and may directly be sent to the fermenters for production of biogas.

Figure 5:
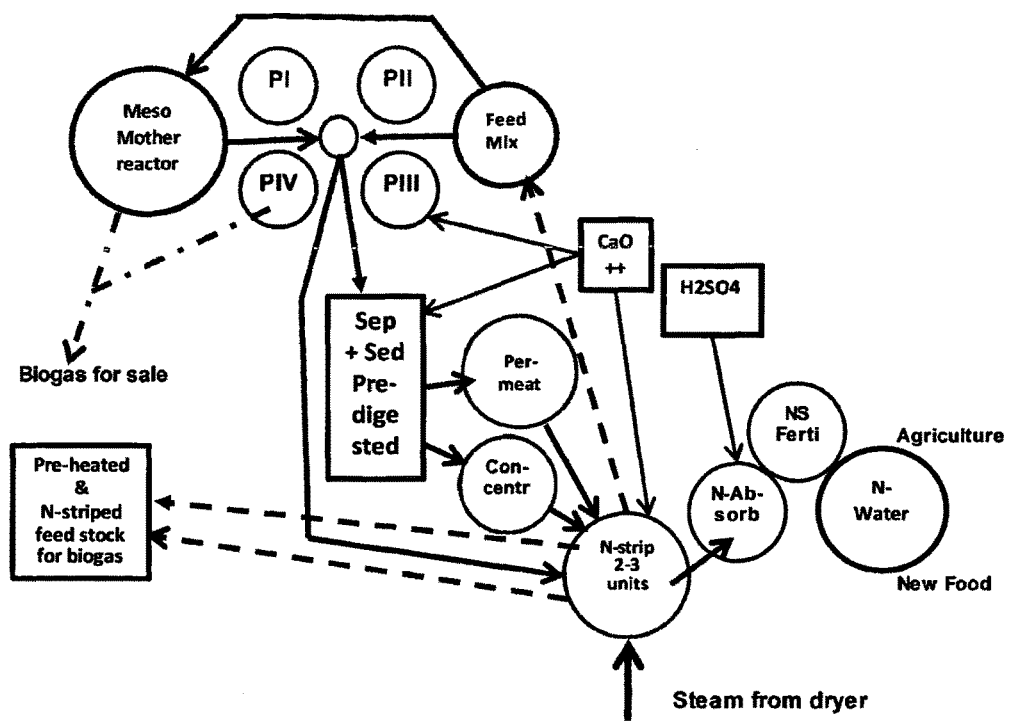
Figure 6:
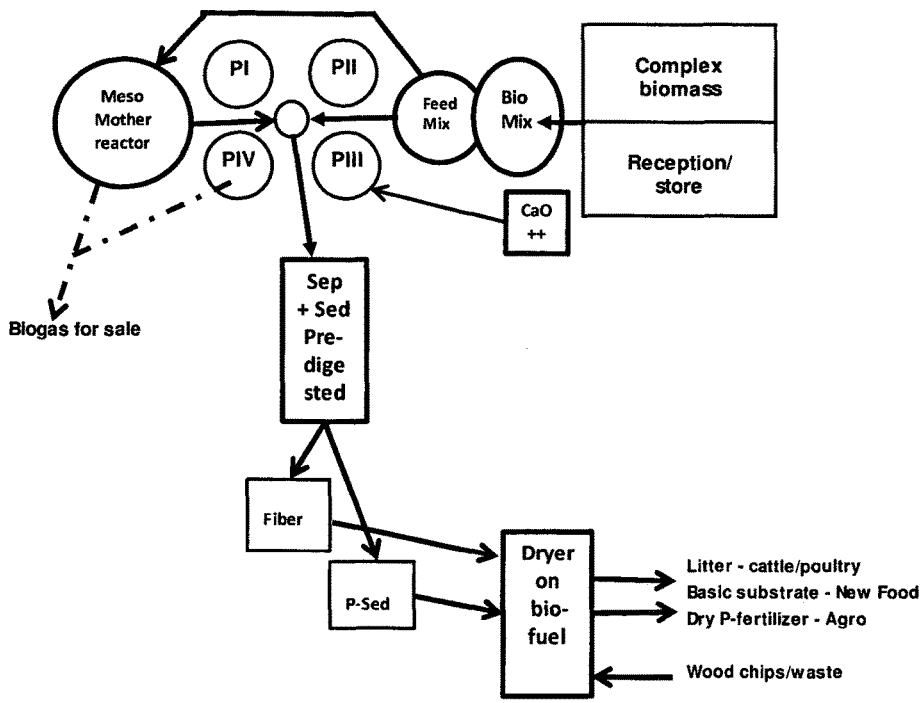

FIGS. 5 & 6 illustrate principles of the handling and processing of a biomass material according to selected methods of the present invention. The biomasses with high dry matter and fiber content are grinded and mixed with more wet types of biomasses in the Bio-Mixer and from there led to the Feed-Mixer where its finally mixed with pre-heated and N-stripped biomass in order to obtain desired dry matter content and temperature before added to meso Mother reactor or pre-reactors (PI-PIV)

Meso Mother reactor is a normal biogas reactor operated at 35-38 dg C, dry matter content ~12-15% and average retention time of 12-15 days. Pre-reactors are smaller batch reactors operated at 35-38 dg C, dry matter content 15-18% and average retention time of 8-10 days+1 day for "killing and empty" and 1 day for "reloading", to obtain the highest possible NH4+-N content before the process is "killed" by adding of CaO.

From pre-reactors the partly degasified biomass is pumped to the Sep & Sed department (separation and sedimentation) and here it is split on desired fractions (fibers, concentrate, P-sediment and permeate) or led directly to the N-strippers. Fiber is dried in the drum dryer for evaporating inorganic N components and water.

Concentrate—high in NH4+-N content—is led to N-strippers and after N-stripping recycled back as valuable and heated feed stock to the Feed-Mixer. P-sediment with high content of P and low in volatile dry matters is dried in the drum dryer and converted to high valuable dry P-fertilizers. Permeate—high in $NH_{4+}$-N content but low in Org N and P content is led to N-strippers and after N-stripping recycled back as first diluting and heating feed stock to the Feed-Mixer.

Figure 7:
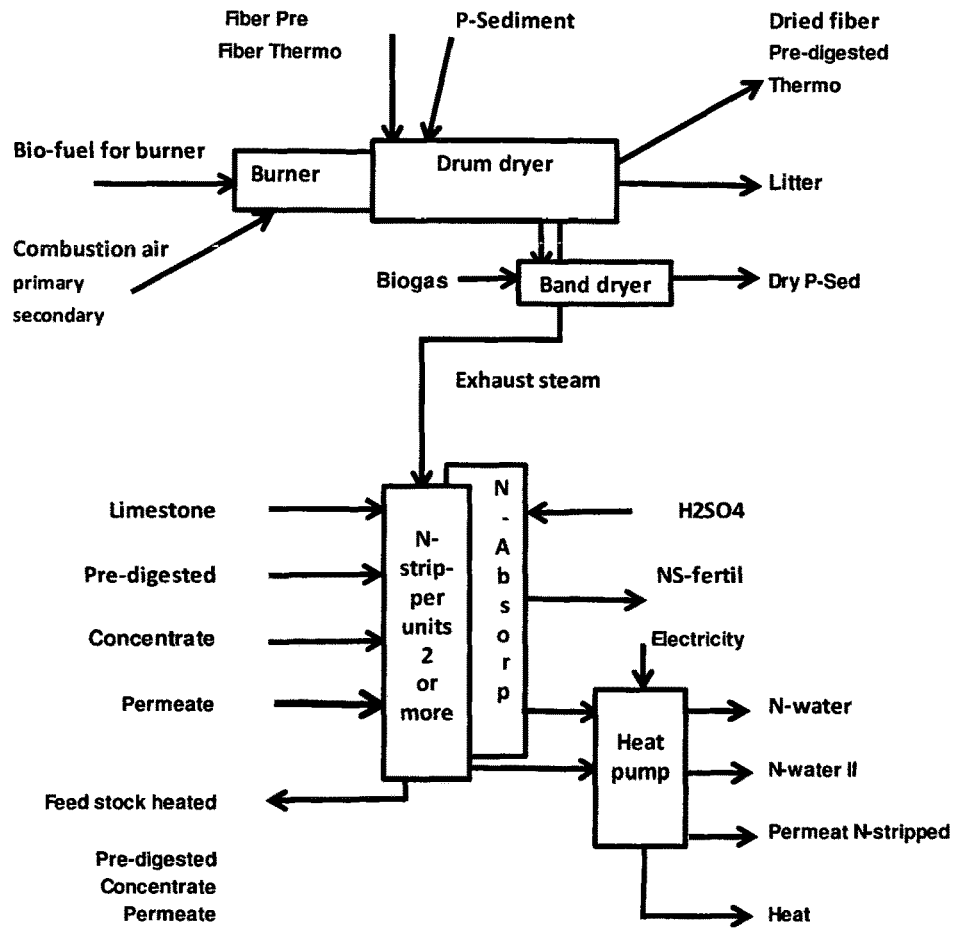

FIG. 7 illustrates the principle of drying a fibrous solid fraction by using a drum dryer fuelled with low quality wood chips and/or wood waste.

Combustion air is taken from the production area and a slightly under pressure is created in order to reduce or preferable eliminate emission of smells and odeurants to the surrounding environment.

The exhaust steam from drum dryer with its content of energy, water, inorganic N components, smelling and volatile substances are injected in pre-digested biomass, concentrate or permeate from Sep & Sed in the N-stripping units and integrated as part of N-stripped and heated biomass.

CoA is added in order to secure optimal N-stripping effect. The stripped gaseous N is absorbed in absorbers and fixed in a liquid NS-fertilizer by adding $H_2SO_4$. The water part from absorbers is collected as N-water and used in new food production and agriculture for irrigation purposes or recycled back to the Feed-Mixer as second diluting and heating feed stock.

Figure 8:
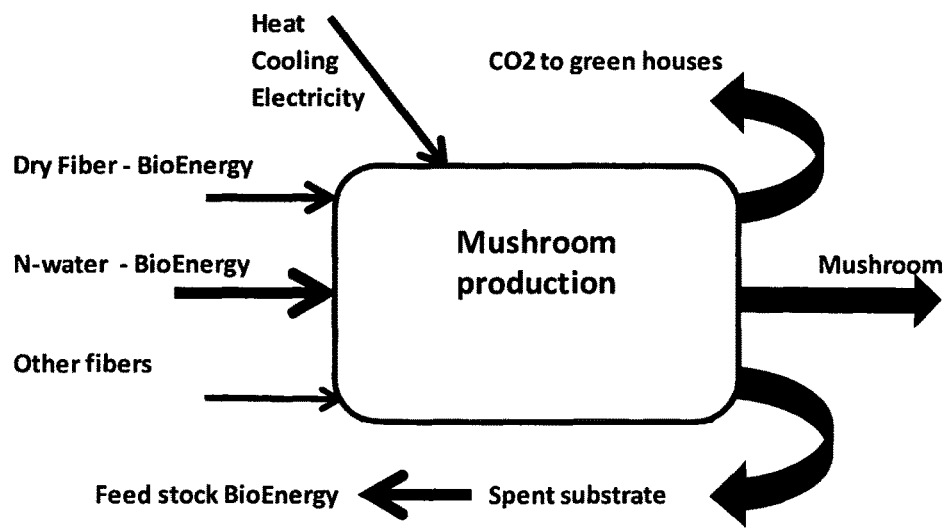

FIG. 8 illustrates a mushroom substrate as a mix of dry fiber from partly degasified biomass, as well as other specific types of fibers and N-water. From the substrate the mushroom takes water and part of nutrients and break down cellulose, hemicellulose, lignin and other components in order to get C. From 1.2 kg of substrate is produced 0.2 kg of exotic mushroom (e.g. Enokitake or Eryngii) and 1 kg of spent mushroom substrate or pre-treated biomass suitable as basic feed stock for biogas.

Figure 9:
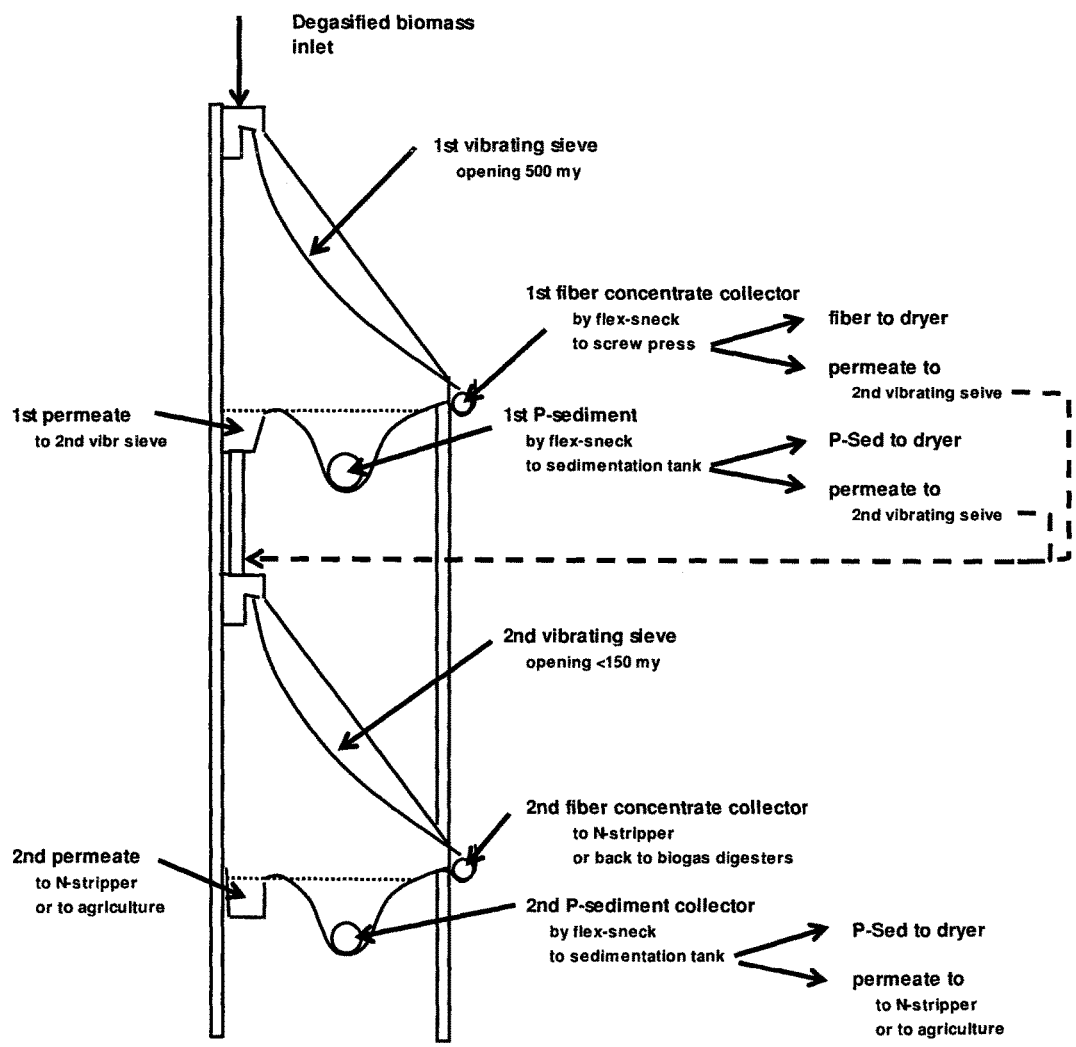

FIG. 9 illustrates one principle for separating and sedimenting a biomass material from an anaerobic fermentation. Partly degasified biomass is pumped to the inlet of the 1$^{st}$ vibrating sieve and separated in a fibrous solid fraction, P-sediment, concentrate and permeate.

Figure 10:
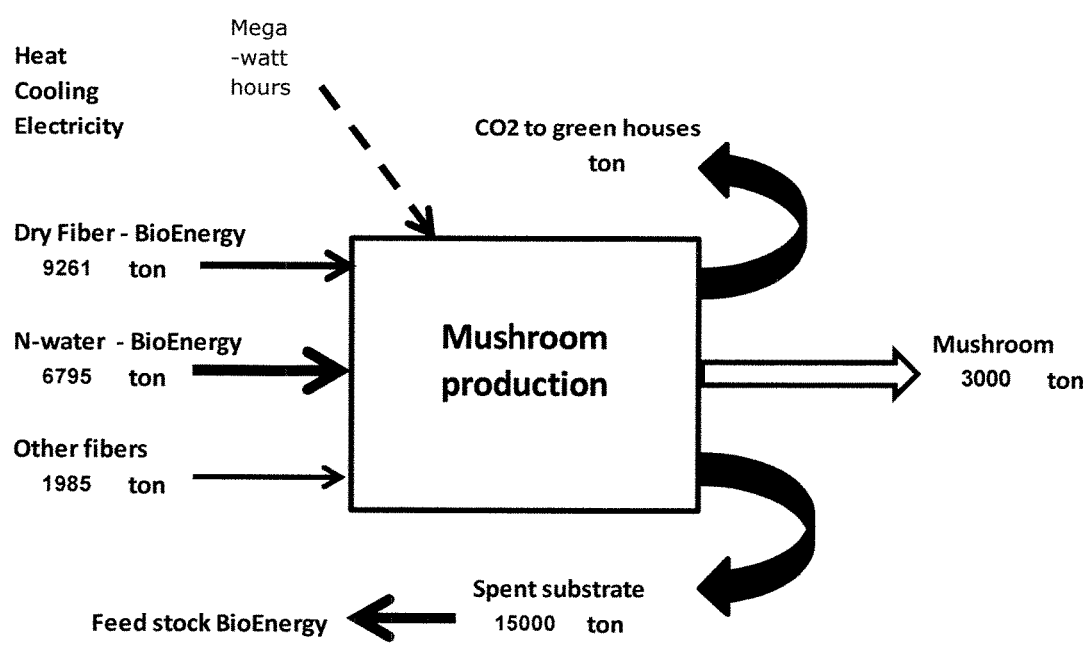

FIG. 10 illustrates the data in Table 6 showing the mushroom production in tons relating to input of dry fiber, N-water—BioEnergy and Other fibers in tons and Heat, Cooling and Electricity input in Megawatt hours (MWh), along with output of Spent substrate and $CO_2$ to green houses in tons (cf. examples).

DETAILED DESCRIPTION OF THE INVENTION

Processing of biomass materials prior to anaerobic biogas fermentation and stripping of ammonia N prior to performing the biogas fermentation is not always sufficient to preclude an undesirable inhibition of biogas-producing bacteria by ammonia not stripped during the pre-treatment step.

There is a need for improving the processing and removal of volatile solids from biomasses prior to such biomasses being subjected to pre-treatment steps e.g. involving thermo-chemical processing steps, such as e.g. lime pressure cooking.

There is also a need for novel and innovative methods for stripping ammonia N from different biomasses such as biomass materials having a high N content.

Furthermore, there is a need for improving the efficiency of anaerobic biogas fermentations and their capability of utilizing macromolecular nutrient constituents selected in particular from cellulose, hemicellulose, lignin and lignocellulose.

The present invention facilitates efficient biomass processing and an increased production of renewable energy from processing and anaerobic fermentation of a wide variety of biomass materials.

Many types of biomass/organic materials have a high energy potential which may be exploited by processing the biomass material. One form of processing an organic material is by performing an anaerobic fermentation resulting in the production of biogas. This process represents a conversion of an energy potential to a readily usable energy source.

There are four key biological and chemical stages of an anaerobic fermentation: hydrolysis; acidogenesis; acetogenesis; and methanogenesis. In order for bacteria under anaerobic conditions to exploit the energy potential of the organic materials used as substrates, macromolecules present in the biomass materials must initially be broken down into their smaller constituent parts. The process of breaking the macromolecular structures initially involves a hydrolysis and/or an oxidation of the macromolecular structures. Breaking down macromolecular constituents present in the biomass materials can advantageously take place e.g. during a pre-treatment processing step prior to anaerobic fermentation and biogas production.

The resulting constituent parts, including monomers and oligomers, such as degraded constituents comprising sugar and/or amino acid residues, can be more readily metabolized by microbial organisms involved in one or more of the steps of acidogenesis; acetogenesis; and methanogenesis.

Acetate and hydrogen produced in the first stages of an anaerobic fermentation can be used directly by methanogens. Other molecules, such as volatile fatty acids (VFAs) with a chain length that is greater than that of acetate, must first be catabolised into compounds that can be directly metabolised by methanogens.

The biological process of acidogenesis further breaks down remaining components by acidogenic (fermentative) bacteria. Here, VFAs are created along with ammonia, carbon dioxide, and hydrogen sulfide, as well as other by-products.

The third stage of an anaerobic fermentation is acetogenesis. Here, simple molecules created through the acidogenesis phase are further digested by acetogens to produce largely acetic acid as well as carbon dioxide and hydrogen.

The final stage of an anaerobic fermentation is that of methanogenesis. Methanogens metabolise intermediate compounds formed during the preceding stages of the anaerobic fermentation, and these compounds are metabolised into methane, carbon dioxide, and water. The aforementioned compounds are the major constituents of a biogas. Methanogenesis is sensitive to both high and low pHs—and methanogenesis generally occurs between pH 6.5 and pH 8.

Remaining, non-digestible organic material that the microbes present in the biogas fermenter may not metabolise, along with any dead bacterial remains, constitutes the digestate from the fermentation in the form of a fibrous solid fraction which can be further separated from fermentations liquids and processed as disclosed herein below.

Apart from having a high energy potential, many biomass materials also have a high content of nitrogen (N). When such organic materials are used as substrates for converting organic materials into bio energy in a bio energy plant, in particular biogas in a biogas plant, the organic N will gradually be converted to ammonia.

The formation of ammonia in a bio energy plant—especially at high levels—represents a problem as many biogas producing bacteria are sensitive to high levels of ammonia—and high ammonia levels in a biogas fermenter will thus reduce or inhibit the production of methane. Ultimately, the formation of high levels of ammonia will kill biogas producing bacteria and inhibit any further biogas formation.

The inhibitory levels of ammonia in a biogas fermenter depend on the conditions used. Under thermophilic fermentation conditions, approx. 3.8 to 4.2 kg ammonia per ton of biomass such as 4.0 kg is considered inhibitory if the biomass has been thermo-chemically pre-treated with added limestone, else in absence of any thermo-chemically pre-treatment the inhibitory level is approx. 3.4 to 3.6 kg ammonia per ton of the biomass such as 3.5 kg. Under mesophilic fermentation conditions the figure is approx. 5.5 to 6.0 kg ammonia per ton of biomass such as 5.8 kg is considered inhibitory if the biomass has been thermo-chemically pre-treated with added limestone, else in absence of any thermo-chemically pre-treatment the inhibitory level is approx. 4.4 to 5.0 kg ammonia per ton of biomass such as 4.7 kg. The biogas fermentation process may be expected to be completely inhibited at ammonia levels of approx. 7.0 kg to 7.5 kg ammonia per ton of biomass such as 7.2 kg ammonia per ton of biomass.

The above-cited ammonia inhibition threshold values are generally taken into consideration when operating commercial biogas plants using conventional organic materials as substrates for the biogas producing bacteria. Many such plants are operated according to a two-step strategy initially adopting thermophile digestion conditions in a first step and mesophile digestion conditions in a separate and subsequent, second step.

The conversion of organic N to ammonia N progresses during an anaerobic fermentation process—i.e. during the process of generating biogas by anaerob fermentation—and a conversion of as much as approx. 60 to 70% of organic N to ammonia N may be expected in accordance with the present invention.

Particular challenges arise when it is desirable to process organic materials having a particularly high organic N content—as inhibitory levels of ammonia during biogas fermentation can be expected to occur relatively early on in the fermentation process due to the high levels of organic N and protein in the organic material to be processed.

Problems related to high organic N content in the basic raw materials are also well known in connection with production of mushroom substrate and normally this is solved by composting and mixing. Doing this means loose of valuable C content from the easy degradable part of volatile solids and in parallel part of N is lost.

Conventional production of substrate is based on the use of poultry manure, deep litter, straw, saw dust and similar types of complex organic waste with high cellulose, hemicellulose, lignin and/or organic N content.

Use of spent mushroom substrate as main feed stock in a conventional biogas plant is due to the high organic N content not possible, but in combination with other types of waste and biomasses, and when using the technologies and processes in the present invention, spent substrate is a valuable feed stock. This is illustrated in the examples.

Examples of organic materials high in N—as evidenced from the above tables—are e.g. sludge from cheese and offal stomach and gut products, and other tabled waste categories/types. However, in order to perform such a mixture one needs to have access to organic materials low in N—and this poses a particular challenge with respect to mixing facilities and the availability in general of particular types of organic materials which will need to be available for "dilution" of organic materials containing high levels of organic N and/or protein. Consequently, it is not always possible to perform such a mixture of different organic materials and even if it should be possible, it imposes certain practical restrictions on the organic materials to be processed by anaerobic fermentation.

The present invention further provides technical solutions to the problem of how to adjust and control moisture content and content of inorganic N as well as organic N and in parallel it provides technical solutions on the problem of how to improve biogas production in a commercial biogas plant. The solutions involves novel and inventive methods for reducing organic N and protein in an organic material further comprising at least one carbon (C) source, either prior to performing an anaerobic fermentation resulting in the production of biogas, or during the progress of an anaerobic fermentation.

The anaerobic fermentation resulting in the production of biogas is followed by one or more processing steps aimed to strip ammonia N from the organic material after to the biogas production from pre-digestion in fermentation facilities, heating and drying. This is illustrated in the examples.

The present invention generally relates to a combined method for manufacturing and recycling a fibrous solid fraction obtained from an anaerobic biogas fermentation for cultivating *Basidiomycete* cells, and subsequently using the spent *Basidiomycete* substrate as a feed stock biomass material in the anaerobic biogas fermentation from which the fibrous solid fraction used for the cultivation of the basiciomycete cells was obtained.

Once the fibrous solid substrate has been obtained from an anaerobic biogas production, one can contact the fibrous solid substrate suitable for cultivating *Basidiomycete* cells with one or more species of *Basidiomycete* cells, or spores, and cultivate said *Basidiomycete* cells, or spores, in said fibrous solid substrate in accordance—in one embodiment—with state-of-the-art cultivation protocols. Examples of such protocols are presented herein elsewhere.

It may be required to add to said thus obtained fibrous solid fraction comprising organic and inorganic nitrogen parts one or more solid and/or liquid supplemental nutrient substrate compositions, thereby generating a final, ready-to-use fibrous solid substrate suitable for cultivating *Basidiomycete* cells. Also, an adjustment of the pH of the liquid parts of the final, ready-to-use fibrous solid substrate suitable for cultivating *Basidiomycete* cells may be required, said adjustment resulting in a final pH value of from about 5.0 to about 7.5.

Accordingly, in one embodiment, the above-cited method further comprises the steps of adding to said fibrous solid fraction comprising organic and inorganic nitrogen parts one or more solid and/or liquid supplemental nutrient substrate compositions, thereby generating a final, ready-to-use fibrous solid substrate suitable for cultivating *Basidiomycete* cells, and/or adjusting the pH of the liquid parts of the final, ready-to-use fibrous solid substrate suitable for cultivating *Basidiomycete* cells may be required, said pH adjustment resulting in a final pH value of from about 5.0 to about 7.5.

The fibrous solid substrate suitable for cultivating *Basidiomycete* cells preferably comprises one or more macromolecular nutrient constituents selected from the group consisting of cellulose, hemicellulose and lignin. Lignocellulose in the form of a feed stock biomass material collectively comprising cellulose, hemicellulose and lignin as macromolecular constituents is another example of biomass materials and macromolecular nutrient constituents difficult for microbial organisms involved in one or more stages of an anaerobic fermentation and biogas production to digest.

The early stages of a biogas fermentation includes an initial stage of hydrolysis of macromolecular nutrient constituents into their basic constituents, or into nutrient constituents which can more readily be metabolized and fermented by the microbial organisms involved in one or more stages of an anaerobic fermentation and biogas production.

Metabolism of nutrient constituents is essential for the production of biogas as no fermentable and energy generating microbial activities can be carried out in the absence of such metabolism.

It is a particular challenge during an anaerobic biogas fermentation that no, or an insufficient hydrolysis takes place of macromolecular nutrient constituents into their basic constituents, or into nutrient constituents which can more readily be metabolized and fermented by the microbial organisms involved in one or more stages of an anaerobic fermentation and biogas production.

Accordingly, the fibrous solid substrate suitable for cultivating *Basidiomycete* cells with one or more species of *Basidiomycete* cells or spores will contain—as a result of an insufficient hydrolysis of macromolecular nutrient constituents into their basic constituents, or into nutrient constituents which can more readily be metabolized and fermented by the microbial organisms involved in one or more stages of an anaerobic fermentation and biogas production—one or more macromolecular nutrient constituents preferably selected from the group consisting of cellulose, hemicellulose and lignin, as well as lignocellulose, a biomass material collectively comprising cellulose, hemicellulose and lignin, as such macromolecular nutrient constituents are difficult, if not impossible, for many, if not all, microbial organisms involved in one or more stages of an anaerobic fermentation and biogas production to digest.

However, many fungal organisms, including many *Basidiomycetes*, are capable of digesting macromolecular nutrient constituents preferably selected from the group consisting of cellulose, hemicellulose and lignin, as well as lignocellulose, as many fungal organisms produce and secrete extracellular enzymes for which said macromolecular nutrient constituents form a substrate.

Accordingly, the *Basidiomycete* cell can be selected from any of the subclasses of Agaricomycetidae, Exobasidiomycetidae, Tremellomycetidae and Ustilaginomycetidae, as long as the *Basidiomycete* cell in question is able to degrade or digest one or more macromolecular nutrient constituents preferably selected from the group consisting of cellulose, hemicellulose and lignin, as well as lignocellulose.

Preferred *Basidiomycete* cells are those which are edible, such as for example a cell selected from the genera of *Agaricus, Lentinula* (*Lentinus*), *Flammulina, Pleurotus*; and *Lyophyllum*. Additionally, and more specifically, the *Basidiomycete* cell can be selected from the species of *Lentinula* (*Lentinus*) edodes; edible *Agaricus* species, such as e.g. *Agaricus blazei* Murill (AbM), a.k.a. *Agaricus subrufescens* Peck, a.k.a. *Agaricus brasiliensis* Wasser, and *Agaricus bisporus, Flammulina velutipes* (Enokitake), *Pleurotus eryngii* (Eryngii), *Pleurotus ostreatus*; and *Lyophyllum shimeji* (Shimeji).

Hence, by recycling once, or more than once, in any order, a) anaerobic biogas fermentation methods exploiting, as a feed stock biomass material, spent fungal substrate, and b) *Basidiomycete* cultivation methods using a fibrous solid fraction from spent, anaerobically fermented biomass material as a substrate for cultivation of said *Basidiomycetes*; one can effectively recycle and utilize more efficiently all of the above-mentioned macromolecular nutrient constituents present in a biomass material to be used for both anaerobic biogas fermentation and the cultivation of fungal species.

Suitable fungal organisms can be selected from organisms constituting the phylum Basidiomycota of the kingdom Fungi, or, in older classification schemes, the class *Basidiomycetes* of the kingdom Plantae, i.e. fungal organisms characterized by bearing the spores on a basidium, including the edible mushrooms described herein elsewhere in more detail. Preferred *Basidiomycetes* are those genera and species producing extracellular enzymes capable of digesting one or more macromolecular nutrient constituents selected from cellulose, hemicellulose, lignin and lignocellulose. Among the genera and species of preferred *Basidiomycetes*, genera and species of *Basidiomycetes* which are edible are particularly preferred.

The combined and sequential re-use of degassed biomass materials and spent mushroom substrates, respectively, is disclosed in various aspects of the present invention as will be clear from the below disclosure of the present invention. Spent fungal substrate diverted to an anaerobic biogas fermentor as described above is supplemented with additional organic waste biomass materials prior to biogas fermentation in order to provide a more optimal feed stock biomass material and in order to ensure continued utilization of suitable and preferred sources of biodegradable and fermentable biomass materials. The solid feed stock biomass materials entering an anaerobic biogas fermenter in this way may be diluted to a suitable content of total solids by adding to said solid feed stock biomass materials any suitable liquid dilution or suspension source, such as e.g. liquids obtained when fragmenting and draining a spent, fermented and degassed biomass material in order to obtain a fibrous solid fraction. Slurries of manures can also be accepted for this purpose.

The fibrous solid substrate having been obtained from an anaerobic biogas fermentation preferably comprises one or more macromolecular nutrient constituents selected from the group consisting of cellulose, hemicellulose and lignin, or in the form of lignocellulose. The fibrous solid substrate can also comprise one or more of such macromolecular constituents, preferably more than one macromolecular constituent, such as two or three macromolecular constituents selected from the group consisting of cellulose, hemicellulose and lignin, wherein said macromolecular constituents are not, or only partly, metabolized by anaerobic bacteria involved in the production under anaerobic fermentation conditions of biogas, and can be at least partly metabolized by said *Basidiomycete* cells contacted with the fibrous solid substrate.

The digestion by in particular extracellular *Basidiomycete* enzymes of said macromolecular constituents results in a hydrolysis and/or an oxidation of at least part of said macromolecular constituents, wherein said hydrolysis and/or oxidation of at least part of said macromolecular constituents in turn generates a substrate capable of being fermented by microbial organisms involved in one or more stages of a biogas fermentation, wherein said microbial organisms involved in said one or more stages of a biogas fermentation preferentially metabolises the hydrolysis and/or oxidation products resulting from the hydrolysis and/or oxidation of said macromolecular constituents, and less preferentially metabolises said macromolecular constituents, including cellulose, hemicellulose and lignin, or wherein said microbial organisms involved in said one or more stages of a biogas fermentation are essentially unable to metabolise said macromolecular constituents, including cellulose, hemicellulose and lignin.

The general lack of hydrolysis of said macromolecular constituents, including cellulose, hemicellulose and lignin, by methanogenic and other anaerobic bacteria involved in the production of biogas under anaerobic fermentation conditions, will result in said macromolecular constituents being present during an anaerobic biogas fermentation during one or more stages of the anaerobic biogas fermentation, including the stages selected from acidogenesis, acetogenesis and methanogenesis.

A Method for Manufacturing a Fibrous Solid Substrate Suitable for Cultivating Fungal Cells In one aspect of the present invention there is provided a method for manufacturing a fibrous solid substrate suitable for cultivating fungal cells, such as *Basidiomycetes*, said method comprising the steps of i) providing a biomass material comprising solid and liquid parts from a biogas fermenter following an anaerobic fermentation and biogas production (a degassed or partly degassed biomass), ii) subjecting the biomass material to one or more separation steps resulting in the provision of a fibrous solid fraction comprising organic and inorganic nitrogen parts and at least one liquid fraction, said liquid fraction optionally comprising solid and liquid organic and inorganic phosphor (P) containing parts, iii) subjecting the fibrous solid fraction to a sanitation treatment comprising one or more sanitation steps, wherein said sanitation treatment a) reduces or eliminates viable microorganisms present in the fibrous solid fraction, and/or b) reduces the contents of volatile nitrogen-containing compounds and/or precursor volatile compounds present in the fibrous solid fraction, iv) obtaining a fibrous solid fraction having a reduced content of nitrogen-containing compounds (and/or an ammonia-stripped and/or sanitised fibrous solid fraction) suitable for use as a fibrous solid substrate for cultivating fungal (such as *Basidiomycete*) cells, and v) optionally adding to said fibrous solid fraction one or more solid and/or liquid supplemental nutrient substrate compositions, thereby generating a fibrous solid substrate suitable for cultivating fungal (such as *Basidiomycete*) cells.

In one embodiment 'a biomass material comprising solid and liquid parts from a biogas fermenter following an anaerobic fermentation and biogas production' according to the invention is a degassed or partly degassed biomass, such as a biomass material which has been subject to anaerobic fermentation thereby producing a biogas and a degassed biomass material comprising organic and inorganic nitrogen parts.

A Method for Cultivating Fungal Cells and/or Spores on a Fibrous Solid Substrate In another aspect of the present invention there is provided a method for cultivating fungal cells, including *Basidiomycete* cells, and/or spores, on a fibrous solid substrate, said method comprising the steps of i) providing fungal (such as *Basidiomycete*) cells and/or spores, ii) providing a fibrous solid substrate for cultivating fungal (such as *Basidiomycete*) cells and/or spores obtained by any of the methods of the present invention disclosed herein, iii) contacting the fungal (such as *Basidiomycete*) cells and/or spores provided in step i) with the fibrous solid substrate provided in step ii), iv) cultivating the fungal (such as *Basidiomycete*) cells and/or spores in said substrate, v) obtaining spent fungal substrate (or spent fungal substrate biomass material), and vi) optionally collecting the spent fungal substrate, wherein said spent fungal substrate is at least partially digested by the cultivation of the fungal cells and is suitable as a feed stock for an anaerobic fermentation and biogas production.

A Method for Recycling Biomass Materials Comprising Organic and Inorganic Nitrogen Parts Selected from Spent Fungal Substrate Biomass Materials and Degassed Fermented Biomass Materials In yet another aspect of the present invention there is provided a method for recycling biomass materials comprising organic and inorganic nitrogen parts selected from 1) spent fungal substrate biomass materials and 2) degassed fermented biomass materials, wherein said method is for a) recycling, more than once, spent fungal substrate biomass material from a fungal cultivation to, and reusing said substrate biomass material in an anaerobic biogas fermentation taking place in an anaerobic biogas fermenter, said fermentation resulting in the production of biogas and a degassed, fermented biomass material for recycling, and/or b) recycling, more than once, a fibrous solid fraction of a degassed fermented biomass material from said anaerobic biogas fermenter to a fungal cultivation facility, and reusing said degassed, fermented biomass material fibrous solid fraction from said anaerobic biogas fermenter to cultivate said fungus, said fungus cultivation resulting in the provision of fungus and a spent fungal substrate biomass material for recycling, said method comprising the steps of i) cycling, more than once, spent fungal substrate biomass material from a fungal cultivation to, and reusing said substrate biomass material in, an anaerobic biogas fermentation taking place in an anaerobic biogas fermenter, said fermentation resulting in the production of biogas and a degassed fermented biomass material suitable for use as a substrate for cultivating fungal cells and/or spores, and ii) cycling, more than once, a fibrous solid fraction of a degassed fermented biomass material from said anaerobic biogas fermenter to a fungal cultivation facility, and reusing said degassed fibrous solid fraction from said anaerobic biogas fermenter to cultivate said fungal cells and/or spores, said fungal cultivation resulting in the provision of fungal cells and/or spores and a spent fungal substrate biomass material suitable for use as a feed stock biomass material in an anaerobic biogas fermentation, iii) fractionating the degassed fermented biomass material by subjecting the degassed fermented biomass material to one or more separation steps as disclosed herein elsewhere, thereby obtaining a) a fibrous solid fraction comprising solid and liquid parts, said fibrous solid fraction further comprising organic and inorganic nitrogen parts, and b) at least one liquid fraction comprising solid and liquid parts, wherein the anaerobic biogas fermenter is optionally supplemented by addition of further anaerobically fermentable organic waste biomass materials, such as in the form of supplementary feed stock biomass materials.

A Method for Controlling the Composition of Nutrients and/or the Moisture Content of a Fibrous Solid Fraction Comprising Organic and Inorganic Nitrogen Parts Suitable for Cultivating Fungal Cells In a still further aspect of the present invention there is provided a method for controlling the composition of nutrients and/or the moisture content of a fibrous solid fraction comprising organic and inorganic nitrogen parts suitable for cultivating fungal such as *Basidiomycete* cells and/or spores, said method comprising the steps of i) providing a biomass material comprising solid and liquid parts from a biogas fermenter following an anaerobic fermentation and biogas production, ii) subjecting the biomass material to one or more separation steps resulting in the provision of a fibrous solid fraction comprising organic and inorganic nitrogen parts and at least one liquid fraction, iii) evaporating, under predetermined conditions, from said fibrous solid fraction an aqueous gas further comprising one or more volatile compounds, iv) obtaining a fibrous solid fraction comprising organic and inorganic nitrogen parts from which said one or more volatile compounds have been removed by evaporation, wherein the fibrous solid fraction is suitable for use as a fibrous solid substrate for cultivating fungal such as *Basidiomycete* cells, and v) optionally adding to the fibrous solid fraction comprising organic and inorganic nitrogen parts obtained in step iv) one or more solid and/or liquid supplemental nutrient substrate compositions, thereby generating a fibrous solid substrate suitable for cultivating fungal such as *Basidiomycete* cells, wherein at least one of said one or more nutrients can be stripped as volatile compounds from said fibrous solid fraction comprising organic and inorganic nitrogen parts by evaporation under said predetermined conditions,
wherein said one or more nutrients are converted into one or more volatile compounds, and
vi) controlling the composition of nutrients and/or the moisture content of the fibrous solid substrate by converting said one or more nutrients into one or more volatile compounds and evaporating said one or more volatile compounds as aqueous gasses from said fibrous solid fraction comprising organic and inorganic nitrogen parts under predetermined evaporation conditions.

A Method for Separating and Drying a Biomass Material Comprising Organic and Inorganic Nitrogen Parts, and Providing a Fibrous Solid Substrate Suitable for Cultivating Fungal Cells The above-cited aspects of the present invention all employ the step of providing a fibrous solid fraction from a degassed, fermented biomass material having been fermented under anaerobic fermentation conditions.

Accordingly, the present invention in yet another aspect provides a method for separating and drying a biomass material comprising organic and inorganic nitrogen parts, and providing a fibrous solid substrate suitable for cultivating fungal such as *Basidiomycete* cells, said method comprising the steps of
i) providing a biomass material comprising solid and liquid parts from a biogas fermenter following an anaerobic fermentation and biogas production,
ii) subjecting the biomass material to one or more separation steps resulting in the provision of a fibrous solid fraction comprising organic and inorganic nitrogen parts and at least one liquid fraction,
iii) subjecting said fibrous solid fraction comprising organic and inorganic nitrogen parts to heating sufficient to evaporate, under predetermined evaporation conditions, volatile compounds present in the fibrous solid fraction comprising organic and inorganic nitrogen parts as volatile compounds, or sufficient to converting volatile precursor compounds into volatile compounds capable of being evaporated under predetermined conditions,
iv) evaporating said one or more volatile compounds under predetermined evaporation conditions characterized at least by heating the fibrous solid fraction to a temperature of at least 70° C. under alkaline pH conditions and at a pressure sufficient to evaporate said volatile compounds, and
  a. providing (obtaining) a) a fibrous solid fraction comprising organic and inorganic nitrogen parts and having an increased content (w/w) of organic nitrogen compounds, a reduced content (w/w) of volatile compounds, or volatile precursor compounds, and a reduced content (w/w) of water, and b) an aqueous gas further comprising one or more volatile compounds, including ammonia,
  thereby separating and drying a biomass biomaterial and providing a fibrous solid substrate suitable for cultivating fungal cells.

A Method for Reducing the Content of Inorganic Nitrogen Compounds in a Fibrous Solid Fraction Comprising Organic and Inorganic Nitrogen Parts In a still further aspect of the present invention there is provided a method for reducing the content of inorganic nitrogen compounds in a fibrous solid fraction comprising organic and inorganic nitrogen parts of a biomass material comprising organic and inorganic nitrogen parts and providing a fibrous solid substrate suitable for cultivating fungal such as *Basidiomycete* cells, said method comprising the steps of
i) providing a biomass material comprising solid and liquid parts from a biogas fermenter following an anaerobic fermentation and biogas production,
ii) subjecting the biomass material to one or more separation steps resulting in the provision of a fibrous solid fraction comprising organic and inorganic nitrogen parts and at least one liquid fraction,
iii) subjecting said fibrous solid fraction comprising organic and inorganic nitrogen parts to heating sufficient to evaporate volatile inorganic nitrogen compounds present in the fibrous solid fraction comprising organic and inorganic nitrogen parts as volatile inorganic nitrogen compounds, or in the form of volatile inorganic nitrogen precursor compounds capable of being evaporated under predetermined conditions,
iv) converting said inorganic nitrogen compounds to gaseous nitrogen containing volatile compounds, including ammonia,
v) evaporating said gaseous nitrogen containing volatile compounds, including ammonia,
wherein said conversion and evaporation generates a fibrous solid fraction comprising organic and inorganic nitrogen parts and having a reduced content of inorganic nitrogen compounds.

A Method for Increasing the Relative Amount of Organic Nitrogen Content of a Fibrous Solid Fraction Comprising Organic and Inorganic Nitrogen Parts of a Biomaterial Following Fermentation and Biogas Production In a still further aspect of the present invention there is provided a method for increasing the relative amount of organic nitrogen content of a fibrous solid fraction comprising organic and inorganic nitrogen parts of a biomass material following fermentation and biogas production, said method comprising the steps of
i) providing a biomass material comprising solid and liquid parts from a biogas fermenter following an anaerobic fermentation and biogas production,
ii) subjecting the biomass material to one or more separation steps resulting in the provision of a fibrous solid fraction comprising organic and inorganic nitrogen parts and at least one liquid fraction,
iii) subjecting said fibrous solid fraction comprising organic and inorganic nitrogen parts to heating sufficient to evaporate volatile inorganic nitrogen compounds present in the fibrous solid fraction comprising organic and inorganic nitrogen parts as volatile inorganic nitrogen compounds, or in the form of volatile inorganic nitrogen precursor compounds capable of being evaporated under predetermined conditions,
iv) converting said inorganic nitrogen compounds to gaseous nitrogen containing volatile compounds, including ammonia,
wherein said conversion and evaporation generates a fibrous solid fraction comprising organic and inorganic nitrogen parts and having an increased, relative amount of organic nitrogen.

A Method for Fractionating a Biomass Material and Obtaining a) a Fibrous Solid Fraction Comprising Solid and Liquid Parts, said Fibrous Solid Fraction Further Comprising Organic and Inorganic Nitrogen Parts, b) at Least One Liquid Fraction Comprising Solid and Liquid Parts, and c) a Phosphor-Containing Fraction or Sediment In yet another aspect of the present invention there is provided a method for fractionating a biomass material and obtaining a) a fibrous solid fraction comprising solid and liquid parts, said fibrous solid fraction further comprising organic and inorganic nitrogen parts, b) at least one liquid fraction comprising solid and liquid parts, and c) a phosphor-containing fraction or sediment, said method comprising the steps of
i) providing a biomass material comprising solid and liquid nitrogen (N) and phosphor-containing parts from a fermenter following an anaerobic fermentation,
ii) subjecting the biomass material to one or more separation steps and obtaining a fibrous solid fraction comprising solid and liquid organic and inorganic nitrogen containing parts, and at least one liquid fraction comprising solid and liquid organic and inorganic phosphor-containing parts,
iii) separating solid and liquid parts of the at least one liquid fraction by fractionation and/or sedimentation, and
iv) obtaining a) a fibrous solid fraction comprising solid and liquid parts comprising organic and inorganic nitrogen parts, b) a first solid, phosphor-containing fraction or sediment suitable for being used as, or added to, a phosphor-containing agricultural fertilizer, and c) a first liquid permeate fraction comprising solid and/or liquid nitrogen and/or phosphor-containing parts.

A Method for Producing a Biogas by Anaerobic Fermentation of a Biomass Material

In a still further aspect of the present invention there is provided a method for producing a biogas by anaerobic fermentation of a biomass material comprising the steps of
i) providing a biomass material suitable for anaerobic fermentation and biogas production,
ii) fermenting the biomass material under anaerobic fermentation conditions, thereby producing a biogas and a degassed biomass material comprising organic and inorganic nitrogen parts,
iii) collecting and/or storing the biogas, said method optionally comprising the further steps of
iv) fractionating the degassed biomass material and obtaining a fibrous solid fraction comprising solid and liquid parts, said fibrous solid fraction further comprising organic and inorganic nitrogen parts, at least one liquid fraction comprising solid and liquid parts, and a phosphor-containing fraction or sediment, said method comprising the further steps of
v) separating solid and liquid parts of the at least one liquid fraction comprising solid and liquid parts, and
vi) obtaining a) a fibrous solid fraction comprising solid and liquid parts, wherein the fibrous solid fraction further comprises organic and inorganic nitrogen parts, b) a first solid, phosphor-containing fraction or sediment suitable for being used as, or added to, a phosphor-containing agricultural fertilizer, and c) a first liquid permeate fraction comprising solid and liquid parts.

A Method for Producing Biogas and Passes Comprising Volatile Nitrogen Containing Compounds by Sequential, Anaerobic Fermentations and Ammonia Stripping In a yet further aspect of the present invention there is provided a method for producing biogas and gasses comprising volatile nitrogen containing compounds by sequential, anaerobic fermentations and stripping at least partly said volatile nitrogen containing compounds, including ammonia, from the fermented biomass materials comprising organic and inorganic parts, said method comprising the steps of
i) providing a first biomass material comprising organic and inorganic nitrogen parts,
ii) performing an initial, anaerobic fermentation of the first biomass material in an anaerobic fermenter,
iii) producing biogas and volatile nitrogen-containing compounds and a fermented, first biomass material under said anaerobic fermentation conditions,
    wherein said initial fermentation of the first biomass material under anaerobic fermentation conditions results in at least partly converting organic nitrogen parts into inorganic nitrogen parts,
    wherein said inorganic nitrogen parts comprise, or are converted into, gasses comprising volatile nitrogen-containing compounds during said initial, anaerobic fermentation,
iv) diverting the first fermented biomass material, and said gasses comprising volatile nitrogen containing compounds formed during said initial, anaerobic fermentation, to a stripper and sanitation tank,
v) stripping at least part of said gasses comprising volatile nitrogen-containing compounds from the first, fermented biomass material in the stripper and sanitation tank by heating to a temperature of at least 70° C. at a pressure sufficient to strip said volatile compounds, thereby obtaining a second biomass material comprising a reduced amount of inorganic nitrogen parts,
vi) diverting said second biomass material having a reduced amount of inorganic nitrogen parts to a further anaerobic fermenter and subsequently fermenting said second biomass material under anaerobic conditions,
vii) producing under anaerobic fermentation conditions biogas and volatile nitrogen-containing compounds and a fermented, second biomass material comprising organic and inorganic nitrogen parts,
viii) wherein said subsequent anaerobic fermentation of the second biomass material results in at least partly converting organic nitrogen parts into inorganic nitrogen parts,
    wherein said inorganic nitrogen parts comprise, or are converted into, gasses comprising volatile nitrogen containing compounds during said subsequent, anaerobic fermentation,
ix) subjecting said fermented, second biomass material to one or more separation steps resulting in the formation of a fibrous solid fraction comprising organic and inorganic nitrogen parts and at least one liquid fraction,
x) subjecting said fibrous solid fraction to a temperature of at least 70° C. at a pressure sufficient to strip said volatile compounds, and stripping volatile nitrogen containing compounds present in the solid fibrous fraction, thereby generating a fibrous solid fraction having a reduced amount of volatile nitrogen containing compounds and inorganic nitrogen precursor volatile compounds, including ammonium,
xi) forming a gaseous fraction comprising nitrogen containing volatile compounds, including ammonia, and having a temperature of at least 70° C., and
xii) diverting said gaseous fraction comprising nitrogen containing volatile compounds, and having a temperature of at least 70° C., to the stripper and sanitation tank of step iv) for stripping of said nitrogen containing volatile compounds,
    wherein the diverted gaseous fraction comprising nitrogen containing volatile compounds, including ammonia, and having a temperature of at least 70° C., contributes to heating the fermented, first biomass material in the stripper and sanitation tank, or a further first biomass material having been diverted to the stripper and sanitation tank from an anaerobic fermenter, and wherein said volatile compounds diverted to said stripper and sanitation tank are converted into solid forms and stored until further use.

A Method for Producing Biogas and Reducing or Eliminating the Emission From a Biogas Fermentation Facility of Undesirable Odorants in the Form of Gasses Comprising Volatile Nitrogen Containing Compounds, and Optionally also Sulphur Containing Compounds, In accordance with this aspect of the present invention there is provided a method for producing biogas and reducing or eliminating the emission from a biogas fermentation facility of undesirable odorants in the form of gasses comprising volatile nitrogen containing compounds, and optionally also sulphur containing compounds, by sequential, anaerobic fermentations and stripping at least partly said volatile nitrogen containing compounds, and optionally also said volatile sulphur containing compounds, including ammonia and, when present, hydrogen sulphide, from the fermented biomass materials comprising organic and inorganic parts, said method comprising the steps of i) providing a first biomass material comprising organic and inorganic nitrogen parts and optionally also sulphur parts, ii) performing an initial, anaerobic fermentation of the first biomass material in an anaerobic fermenter, iii) producing biogas and volatile nitrogen and sulphur containing compounds, and a fermented, first biomass material,
    wherein said initial anaerobic fermentation of the first biomass material results in at least partly converting organic nitrogen parts into inorganic nitrogen parts,
    wherein said inorganic nitrogen parts comprise, or are converted into gasses comprising volatile nitrogen containing compounds during said initial anaerobic fermentation,
    wherein said sulphur parts, when present, comprise, or are converted into, gasses comprising volatile sulphur containing compounds during said initial, anaerobic fermentation, iv) diverting the first fermented biomass material, and said gasses comprising volatile nitrogen and optionally sulphur containing compounds formed during said initial, anaerobic fermentation, to a stripper and sanitation tank for stripping of said volatile compounds, v) stripping at least part of said gasses comprising volatile nitrogen and optionally sulphur containing compounds by heating, to a temperature of at least 70° C. at a predetermined pressure sufficient stripping said volatile compounds, the contents of the stripper and sanitation tank, thereby obtaining a second biomass material comprising a reduced amount of inorganic nitrogen and optionally sulphur parts, vi) diverting said second biomass material having a reduced amount of inorganic nitrogen and optionally sulphur parts to a further anaerobic fermenter and subsequently fermenting said second biomass material under anaerobic conditions, vii) producing biogas and volatile nitrogen and optionally also sulphur containing compounds, and a fermented, second biomass material comprising organic and inorganic nitrogen parts under said anaerobic fermentation conditions,
    wherein said subsequent anaerobic fermentation of the second biomass material results in at least partly converting organic nitrogen parts into inorganic nitrogen parts,
    wherein said inorganic nitrogen parts comprise, or are converted into, gasses comprising volatile nitrogen containing compounds during said subsequent, anaerobic fermentation,
    wherein said sulphur parts, when present, comprise, or are converted into, gasses comprising volatile sulphur containing compounds during said subsequent, anaerobic fermentation, viii) subjecting said fermented, second biomass material to one or more separation steps resulting in the formation of a fibrous solid fraction comprising organic and inorganic nitrogen parts and at least one liquid fraction, ix) subjecting said fibrous solid fraction to a heating and drying treatment by heating said solid fraction to a temperature of at least 70° C. at a pressure sufficient to strip said volatile compounds, and stripping volatile nitrogen containing compounds, and optionally also sulphur containing compounds, present in the solid fibrous fraction,
    thereby generating a dried fibrous solid fraction having a reduced amount of volatile nitrogen containing compounds, including ammonium and inorganic nitrogen precursor volatile compounds, and optionally also a reduced amount of sulphur containing volatile compounds, e.g. hydrogen sulphide,
    wherein the heating and drying treatment exploits primary and secondary combustion air sources, including exhaust air sources, present in or generated in the biogas fermentation facility as a result of performing said heating and drying process, wherein said primary and secondary combustion air sources are also diverted to said stripper and sanitation tank for conversion and/or collection as solids,
    wherein the exploitation of primary combustion air sources from the biogas fermentation facility results in generating a negative pressure in the biogas fermentation facility space, which negative pressure prevents or contributes to presenting any undesirable odorants from escaping the biogas fermentation facility, x) forming a gaseous fraction comprising nitrogen containing volatile compounds, including ammonia, and having a temperature, of at least 70° C. at a pressure sufficient to form said gaseous fraction, xi) diverting said gaseous fraction comprising nitrogen containing volatile compounds, including ammonia, and optionally also sulphur containing volatile compounds, and having a temperature of at least 70° C. at said predetermined pressure, to the stripper and sanitation tank of step iv) for stripping of said nitrogen containing volatile compounds and optionally also said sulphur containing volatile compounds,
    wherein the diverted gaseous fraction having a temperature of at least 70° C. contributes to heating the fermented first biomass material in the stripper and sanitation tank, and/or the further first biomass material having been diverted to the stripper and sanitation tank, and
    wherein said volatile compounds diverted to said stripper and sanitation tank are converted into solid forms and stored until further use, and xii) reducing or eliminating the emission from a biogas fermentation facility of undesirable odorants in the form of gasses comprising volatile nitrogen containing compounds, and optionally also volatile sulphur containing compounds, by performing said sequential anaerobic fermentations in a closed system and stripping at least partly said volatile nitrogen containing compounds, and optionally also said volatile sulphur containing compounds,
such as ammonia and hydrogen sulphide respectively, from the fermented biomass materials comprising organic and inorganic parts,
wherein the conversion into solid forms of said volatile compounds diverted to said stripper and sanitation tank contributes to the reduction or elimination of the emission from the biogas fermentation facility of undesirable odorants in the form of gasses comprising said volatile compounds.

A Method for Sequential Fermentation of a Biomass Material

In yet another aspect of the present invention there is provided a method for sequential fermentation of a biomass material, said method comprising the steps of
i) fermenting a biomass material by anaerobic batch fermentation, wherein the anaerobic batch fermentation results in the production of nitrogen containing volatile compounds, including ammonia,
ii) removing said nitrogen containing volatile compounds from the batch fermented biomass material, thereby reducing the contents of nitrogen containing volatile precursor compounds capable of being converted into nitrogen containing volatile compounds during said anaerobic batch fermentation, and generating an anaerobic batch fermented biomass material having a reduced amount of inorganic nitrogen precursor volatile compounds,
iii) obtaining an anaerobic batch fermented biomass material having a reduced content of nitrogen containing volatile compounds and comprising lignocellulose and additional macromolecular constituents not digested during said anaerobic batch fermentation,
iv) diverting the anaerobic batch fermented biomass material from the batch fermentation facility to a fungal cultivation facility and employing the batch fermented biomass material, or a solid fibrous fraction thereof having a reduced amount of inorganic nitrogen precursor volatile compounds, as a substrate for cultivating one or more fungal species,
v) cultivating said one or more fungal species in said substrate, wherein said cultivation results in the hydrolysis and/or oxidation of at least part of said lignocellulose and/or said additional macromolecular constituents not digested during said batch fermentation and the formation of a spent fungal substrate material,
vi) generating a spent fungal substrate material comprising macromolecular hydrolysis and/or oxidation products obtained by fungal digestion of said lignocellulose and/or said additional macromolecular constituents not digested during said anaerobic batch fermentation,
vii) diverting the spent fungal substrate material from the facility for cultivating one or more fungal species to a facility for continuous, anaerobic biogas fermentation and employing the macromolecular hydrolysis and/or oxidation products in said spent fungal substrate material obtained by fungal digestion of said lignocellulose and/or said additional macromolecular constituents not digested during said anaerobic batch fermentation as a substrate for microbial organisms involved in the continuous anaerobic biogas fermentation, and
viii) performing a continuous, anaerobic biogas fermentation using said spent fungal substrate material supplemented with one or more further biomass materials as a substrate for producing said biogas during a continuous, anaerobic biogas fermentation.

A Method for Obtaining a Feed Stock Biomass Material Suitable for use in Anaerobic Biogas Fermentation In a further aspect of the present invention there is provided a method for obtaining a feed stock biomass material suitable for use in anaerobic fermentation and biogas production, said method comprising the steps of
i) providing a first fermented biomass material as a substrate for cultivating one or more fungal species, such as *Basidiomycetes*, wherein said first fermented biomass material comprises one or more macromolecular nutrient constituents selected from the group consisting of cellulose, hemicellulose, and lignin,
ii) cultivating said one or more fungal species in said substrate,
wherein said fungal species cultivation converts the macromolecular nutrient constituents present in said substrate to lower molecular weight nutrient constituents,
wherein the cultivation of said fungal species in said substrate generates a first spent fungal species substrate,
iii) diverting said first spent fungal species substrate to an anaerobic biogas fermenter as a contribution to a feed stock biomass material,
iv) diverting one or more further biomass materials to said anaerobic biogas fermenter, such as organic waste biomass materials comprising one or more macromolecular nutrient constituents selected from the group consisting of cellulose, hemicellulose and lignin,
v) performing an anaerobic biogas fermentation by using said first spent fungal species substrate and said one or more further biomass materials as a feed stock biomass material, and
vi) producing biogas by fermentation of said feed stock under anaerobic fermentation conditions,
wherein said anaerobic biogas fermentation generates a fermented, second biomass material.

The method in one embodiment comprises the further step of fractionating said fermented, second biomass material into solid and liquid fractions and obtaining a solid fibrous fraction comprising solid and liquid parts.

The method in one embodiment further comprises the additional steps of
i) providing said second fermented biomass material, or a solid fibrous fraction thereof, as a substrate for cultivating one or more fungal species, wherein said second fermented biomass material, or a solid fibrous fraction thereof, comprises one or more macromolecular nutrient constituents selected from the group consisting of cellulose, hemicellulose, and lignin
ii) cultivating said one or more fungal species in the substrate provided in step i), wherein said cultivation converts, by hydrolysis, oxidation, or otherwise, macromolecular nutrient constituents present in said substrate to lower molecular weight nutrient constituents
wherein said conversion of said macromolecular nutrient constituents is obtained when said fungal species are metabolizing said macromolecular constituents,
wherein the cultivation of said fungal species in said substrate provided in step i) generates a second spent fungal species substrate having a different composition compared to the composition of the substrate provided in step i),
iii) diverting said second spent fungal species substrate to an anaerobic biogas fermenter as a contribution to a feed stock biomass material,
iv) diverting one or more further biomass materials, preferably organic waste biomass comprising one or more macromolecular nutrient constituents selected from the group consisting of cellulose, hemicellulose and lignin, to said anaerobic biogas fermenter as a further contribution to the formation of a feed stock biomass material suitable as a substrate for producing said biogas during an anaerobic biogas fermentation, v) performing an anaerobic biogas fermentation by using said second spent fungal species substrate and said one or more further biomass materials, preferably organic waste biomass materials, as a feed stock biomass material, and vi) producing biogas by fermentation of said feed stock under anaerobic fermentation conditions, wherein said anaerobic biogas fermentation additionally generates a fermented, third biomass material.

The method in one embodiment further comprises the additional further steps of i) providing said third fermented biomass material, or a solid fibrous fraction thereof, as a substrate for cultivating one or more fungal species, wherein said third fermented biomass material, or a solid fibrous fraction thereof, comprises one or more macromolecular nutrient constituents selected from the group consisting of cellulose, hemicellulose, and lignin, ii) cultivating said one or more fungal species in the substrate provided in step i), wherein said cultivation converts, by hydrolysis, oxidation, or otherwise macromolecular nutrient constituents present in said substrate to lower molecular weight nutrient constituents, wherein said conversion of said macromolecular nutrient constituents is obtained when said fungal species are metabolizing said macromolecular constituents, wherein the cultivation of said fungal species in said substrate provided in step i) generates a third spent fungal species substrate having a different composition compared to the composition of the substrate provided in step i), iii) diverting said third spent fungal species substrate to an anaerobic biogas fermenter as a contribution to a feed stock biomass material, iv) diverting one or more further biomass materials, preferably organic waste biomass comprising one or more macromolecular nutrient constituents selected from the group consisting of cellulose, hemicellulose and lignin, to said anaerobic biogas fermenter as a further contribution to the formation of a feed stock biomass material suitable as a substrate for producing said biogas during an anaerobic biogas fermentation, v) performing an anaerobic biogas fermentation by using said third spent fungal species substrate and said one or more further biomass materials, preferably organic waste biomass materials, as a feed stock biomass material, and vi) producing biogas by fermentation of said feed stock under anaerobic fermentation conditions, wherein said anaerobic biogas fermentation additionally generates a fermented, fourth biomass material.

The cyclical reuse of a) spent fermentation substrate in the form of fermented biomass material, or a solid fibrous fraction thereof, for cultivation of fungal species, and b) spent fungal species substrate for performing an anaerobic biogas fermentation, respectively, can be further repeated one or more times, wherein, preferably, the fermented biomass material, or a solid fibrous fraction thereof, provided step i) of said different cycles of the method as a substrate for cultivating one or more fungal species is obtained from different batch fermentations, and wherein said different batch fermentations further comprise stripping by evaporation volatile nitrogen containing compounds, including ammonia, from said batch fermented biomass materials, thereby providing a substrate for cultivating said one or more fungal species which has a lower amount of inorganic nitrogen compounds compared to a substrate from which no volatile nitrogen containing compounds had been removed prior to cultivation of said fungal species.

The anaerobic biogas fermentation to which the spent fungal species substrates and the one or more further biomass materials, preferably organic waste biomass materials, are diverted, is preferably the same, continuous anaerobic biogas fermentation, and preferably the spent anaerobic fermentation biomass materials from said continuous anaerobic biogas fermentation are being continuously diverted from said anaerobic biogas fermenter and combined with spent biomass materials from said batch fermentations prior to said spent biomass materials being used a substrates for fungal cell cultivation.

In one embodiment the spent biomass materials is separated, dried and/or fractionated by a method for separation and drying of a biomass material according to the present invention.

A Method for Sequentially and Differentially Fermenting a Biomass Material Comprising Different Bioenergy Sources In a still further aspect of the present invention there is provided a method for sequentially and differentially fermenting a biomass material comprising different bioenergy sources, said method comprising the steps of i) fermenting one or more first fermentable bioenergy sources forming part of a fermentable biomass material further comprising one or more additional fermentable bioenergy sources, ii) producing a) one or more fermentation products comprising, or selected from, biogas and gasses comprising volatile nitrogen containing compounds, and b) a first fermented biomass material, by preferentially fermenting said one or more first, fermentable bioenergy sources, wherein said first fermented biomass material comprises a reduced amount of said one or more first, fermentable bioenergy sources, and essentially all, or at least the majority of, said one or more additional fermentable bioenergy sources, iii) diverting said first, fermented biomass material to a fungal cultivation facility and cultivating fungal cells in said first fermented biomass material, iv) producing a) fungal cell biomass, and b) a spent fungal substrate biomass material, by metabolizing said one or more additional, fermentable bioenergy sources and any remaining, first fermentable bioenergy source, wherein said spent fungal substrate biomass material comprises a reduced amount of said one or more additional, fermentable bioenergy source and first, fermentable bioenergy sources generated by fungal cell metabolism of said one or more additional, fermentable bioenergy sources, v) harvesting said fungal cell biomass, vi) diverting said spent fungal substrate biomass material to an anaerobic biogas fermenter as a feed stock biomass material, vii) supplementing the feed stock biomass materials in said anaerobic biogas fermenter with one or more organic waste biomass materials, wherein said one or more organic waste biomass materials comprises fermentable bioenergy sources selected from first bioenergy sources and/or one or more additional bioenergy sources, viii) fermenting said combined feed stock biomass materials under anaerobic fermentation conditions, and ix) producing a) one or more fermentation products comprising, or selected from, biogas and gasses comprising volatile nitrogen containing compounds, and b) a further first fermented biomass material, by preferentially fermenting said one or more first fermentable bioenergy sources present in the combined feed stock biomass materials, wherein said further first, fermented biomass material comprises a reduced amount of said one or more first, fermentable bioenergy sources, and essentially all, or at least the majority of, said one or more additional fermentable bioenergy sources.

The method in one embodiment further comprises the additional steps of x) producing a) additional fungal cell biomass, and b) additional spent fungal substrate biomass material, by metabolizing said one or more additional, fermentable bioenergy sources and any remaining, first fermentable bioenergy source, wherein said additional spent fungal substrate biomass material comprises a reduced amount of said one or more additional, fermentable bioenergy source and first, fermentable bioenergy sources generated by fungal cell metabolism of said one or more additional, fermentable bioenergy sources, xi) harvesting said additional fungal cell biomass, xii) diverting said additional spent fungal substrate biomass material comprising first, fermentable bioenergy sources generated by fungal cell metabolism of said one or more additional, fermentable bioenergy sources to an anaerobic biogas fermenter as a feed stock biomass material, xiii) producing a) one or more further fermentation products comprising, or selected from, biogas and gasses comprising volatile nitrogen containing compounds, and b) additional first fermented biomass material, by preferentially fermenting said one or more first, fermentable bioenergy sources present in the combined feed stock biomass materials, wherein said additional first, fermented biomass material comprises a reduced amount of one or more first, fermentable bioenergy sources, and essentially all, or at least the majority of, one or more additional fermentable bioenergy sources.

The fermentable biomass material provided in step i) is in one embodiment a partly degassed biomass material obtained by performing an initial, anaerobic fermentation resulting in the production of a gaseous fraction comprising ammonia and biogas. Accordingly, the fermentable biomass material is preferably obtained from different batch fermentations, and the method may comprise the further step of stripping by evaporation volatile nitrogen containing compounds, including ammonia, from said fermented biomass materials, thereby providing a substrate for cultivating said one or more fungal species having a lower amount of inorganic nitrogen compounds compared to a substrate from which no volatile nitrogen containing compounds have been removed prior to cultivation of said fungal species.

The anaerobic biogas fermentation to which the spent fungal species substrates and the one or more further biomass materials, preferably organic waste biomass materials, are diverted, is preferably the same, continuous anaerobic biogas fermentation, and preferably the spent anaerobic fermentation biomass materials from said continuous anaerobic biogas fermentation are being continuously diverted from said anaerobic biogas fermenter and combined with spent biomass materials from said batch fermentations prior to said spent biomass materials being used a substrates for fungal cell cultivation.

In one embodiment the spent biomass materials is separated, dried and/or fractionated by a method for separation and drying of a biomass material according to the present invention.

A Method for Producing and Collecting First and Second Volatile Compounds through Sequential Fermentations of a Fermentable Biomass Material It is an aspect of the present invention to provide a method for producing and collecting first and second volatile compounds through sequential fermentations of a fermentable biomass material, said method comprising the steps of i) performing a first anaerobic fermentation of a first fermentable biomass material, such as in one or more pre-fermentation facility or first fermentation facility unit(s), thereby obtaining a first fermented biomass material, and producing and collecting first volatile nitrogen-containing compounds, ii) separating at least partly the first fermented biomass material from the first volatile nitrogen-containing compounds and obtaining a separated, first fermented biomass having a reduced content of first volatile nitrogen-containing compounds, and/or a reduced content of carbon and nitrogen-containing precursor compounds capable of being converted into first volatile carbon and nitrogen containing compounds during a fermentation, iii) diverting the separated, first fermented biomass to a second fermentation facility for producing second volatile methane-containing compounds, and iv) performing a second anaerobic fermentation of the separated, first fermented biomass, optionally supplemented with additional organic waste biomass material, in the second fermentation facility, thereby obtaining a second fermented biomass material, and producing and collecting at least second volatile methane-containing compounds.

It is understood that the method for producing and collecting first and second volatile compounds through sequential fermentations of a fermentable biomass material, as outlined herein above, can be combined with any of the other methods defined according to the invention.

In one embodiment at least some of said first volatile nitrogen-containing compounds produced from the fermentation of the first fermentable biomass material have an inhibitory effect on the formation of second volatile methane-containing compounds during the fermentation of the first fermentable biomass material in said one or more pre-fermentation facility or first fermentation facility unit(s), and an increased amount of second volatile methane-containing compounds are produced from the anaerobic fermentation of the separated, first fermented biomass in the second anaerobic fermentation facility due to the stripping of first volatile nitrogen-containing compounds from said first fermentable biomass material in said one or more pre-fermentation facility or first fermentation facility unit(s).

In one embodiment the first volatile compounds comprises gaseous ammonia. In one embodiment the second volatile compounds, the second volatile methane-containing compounds, collectively form a gas comprising methane, such as a gas comprising more than 50% methane, such as more than 60% methane, such as more than 70% methane, such as more than 80% methane, such as more than 90% methane, such as more than 95% methane, or such as more than 99% methane, such as a biogas.

In one embodiment,
the formation of first volatile nitrogen-containing compounds inhibit the formation of second volatile methane-containing compounds during the first and/or second fermentation, and/or
at least about 20%, such as 30%, such as 40%, such as at least about 50%, of organic N in the biomass is converted to ammonia N during the first anaerobic fermentation, and/or
ammonia N stripped from the organic material in the pre-fermentors/pre-reactors are diverted to a stripper and sanitation tank and/or to an absorption column for absorption of the stripped ammonia N.

In one embodiment,
the method further comprises the step of mixing the complex biomass in a first mixing tank prior to the first fermentation in the pre-fermentation or first facility unit(s), wherein said mixing in one embodiment further comprises addition of lime, and/or
the sequential fermentation of the fermentable biomass material comprises at least three separate fermentation steps, and/or
the first fermentation is conducted under thermophilic conditions or mesophilic conditions, and/or
the temperature for the fermentation of the first fermentable biomass material is in the range of from 25° C. to 55° C., such as from 25° C. to 28° C., 28° C. to 30° C., 30° C. to 32° C., 32° C. to 35° C., 35° C. to 38° C., 38° C. to 42° C., 42° C. to 45° C., 45° C. to 48° C., 48° C. to 52° C., 52° C. to 55° C., and/or
the fermentation of the first fermentable biomass material is performed until a substantial amount of first volatile compounds is produced, wherein a substantial amount of first volatile compounds is an amount which has an inhibitory effect on the microbial organisms performing the fermentation and effectively inhibits growth and/or metabolism of said microbial organisms.

The separation of first fermented biomass and first volatile nitrogen-containing compounds may be performed in various ways according to the present invention.

In one embodiment the step of separating first volatile compounds from the first, fermentable biomass material includes diverting the first fermented biomass to a stripper and sanitation tank for stripping said first volatile compounds, and heating the first fermented biomass material, thereby producing a separated, first biomass material. The stripping-off of the first volatile compound includes ammonia stripping.

In one embodiment
the separated, first fermented biomass is diverted to a pressure unit and subjected to a thermal hydrolysis, thereby producing an at least partly hydrolyzed, fermentable biomass, and/or
the first fermented biomass is diverted to a fermentation facility comprising thermophilic and/or mesophilic fermenters for biogas production, and/or
the method comprises the further step of diverting non-complex biomass material to the pressure unit and subjecting the combined biomass materials in the pressure unit to a thermal hydrolysis, thereby producing an at least partly hydrolysed fermentable biomass, and diverting the at least partly hydrolyzed, fermentable biomass to the second fermentation facility, and/or
the method further comprises the step of at least partly stripping-off first volatile compounds formed during the thermal hydrolysis.

In one embodiment the thermal hydrolysis occurs under predetermined alkaline conditions, optionally achieved by addition of sufficient lime to reach a pH in the range of from about 9 to about 12.

In one embodiment the hydrolysis of the biomass material in the pressure unit is performed at a temperature in the range of from 100° C. to preferably less than 250° C., under a pressure of from about 2 to preferably less than 20 bar, and with an operation time ranging of preferably less than 60 minutes, or until the biomass is suitably hydrolysed.

In one embodiment the at least partly hydrolyzed biomass from the pressure unit is diverted to the pre-fermentation or first fermentation facility unit(s) for further fermentation. In one embodiment said at least partly hydrolyzed and further fermented biomass is further diverted to ammonia stripping in a stripper and sanitation unit.

In one embodiment the further fermentation is followed by a further thermal hydrolysis in the pressure unit for producing a further and even more hydrolyzed biomass.

In one embodiment the method further comprises fermenting the at least partly hydrolyzed and optionally further fermented biomass in the second fermentation facility for producing a biogas comprising second volatile compounds.

In one embodiment fermentation in the second fermentation facility comprises i) subjecting the at least partly hydrolyzed biomass or the further hydrolyzed biomass to first fermentation conditions resulting in the formation of a first conditioned fermented biomass; and ii) subjecting the first conditioned fermented biomass to a fermentation under a second set of conditions for producing a fermentation biomass and second volatile compounds. In one embodiment the first conditions comprise thermophilic conditions and the second conditions comprise mesophilic conditions. In one embodiment the first conditions comprises mesophilic conditions and the second conditions comprises thermophilic conditions.

In one embodiment at least part of the first conditioned, fermented biomass is diverted to a first mixing unit and/or to the pre-fermentation facility units. In one embodiment at least part of the fermented biomass is diverted to a first mixing unit and/or to one or more of the pre-fermentation facility units.

Also provided is a method for producing a first volatile compound through fermentation of a biomass material comprising solid and/or liquid parts, the method comprising i) receiving the biomass material in one or more pre-fermentation facility unit(s); and ii) performing a first fermentation of the biomass material in the one or more pre-fermentation facility unit(s) for producing a first fermented biomass material and at least the first volatile compound until a substantial amount of the first volatile compound is produced.

Also provided is a method for identifying a complex biomass, the method comprising computing content of organic Nitrogen in relation to the total content of the biomass material; and categorizing the biomass material as a complex biomass if the biomass material comprises a high percentage of organic Nitrogen.

The invention in a further aspect is directed to a sequential fermentation facility plant for fermenting a fermentable biomass and suitably adapted for generating at least first and second volatile compounds, said fermentation facility plant comprising i) one or more pre-fermentation facility unit(s) for performing a first fermentation of the fermentable biomass material, ii) a separation unit operably connected to the pre-fermentation facility unit(s) for separating, at least partly, first fermented biomass material from first volatile compounds, thereby obtaining a separated, first fermented biomass comprising a reduced content of first volatile compounds and/or a reduced content of carbon and nitrogen containing precursor compounds capable of being converted during a fermentation to first volatile compounds; and iii) a second fermentation facility operably connected to the separation unit for performing a fermentation of the separated, first fermented biomass, thereby producing a further fermented biomass material and second volatile compounds.

In one embodiment, said separation unit comprises an N-stripper unit for stripping first volatile compounds from the fermented biomass material fermented in the one or more pre-fermentation facility unit(s), and/or said N-stripper unit is connected to an absorption unit for absorbing and condensing first volatile compounds stripped from the first fermented biomass material, and/or said separation unit comprises a sanitation unit for sanitizing the first fermented biomass material, and/or said pre-fermentation facility unit(s) and the separation unit are connected so that the first fermented biomass material is diverted from the pre-fermentation facility unit(s) to the separating unit, and/or said fermentation facility plant further comprises a pressure unit adapted to perform a thermal hydrolysis, optionally under predetermined alkaline conditions, of the separated, first fermented biomass material, wherein the pressure unit is operably connected to both the separation unit and to the second fermentation facility, and/or said fermentation facility plant further comprises a stripper tank connected to the pressure unit for stripping first volatile compounds from hydrolyzed biomass, wherein the stripper tank is connected to an absorption unit for absorbing and condensing stripped first volatile compound, and/or said separation unit is connected to the pressure unit and/or to the second fermentation facility so that the first fermented biomass material stripped off the first volatile compounds can be diverted to the pressure unit and/or to the second fermentation facility, and/or said fermentation facility plant further comprise connections between the pre-fermentation facility unit(s), the separation unit and the pressure unit, said pressure unit is connected with the second fermentation facility for diverting at least partly hydrolyzed biomass at least partly stripped off first volatile compounds to the second fermentation facility, and/or a plurality of pre-fermentation facility unit(s) are operably connected and wherein the second fermentation facility comprises a further plurality of operably connected fermentation units, and/or said fermentation facility units are connected to the pre-fermentation facility unit(s) and/or to a first mixing tank for allowing diversion of the first fermented biomass from the pre-fermentation facility and/or diversion of biomass from the first mixing tank, and/or the fermentation facility is adapted to receive biomass from a reception tank using first reception connectors, the pressure unit is adapted to receive biomass from the reception tank using second reception connectors, and the pre-fermentation facility unit is adapted to receive biomass from the reception tank/the first mixing tank using third reception connector, and/or the pre-fermentation facility unit(s) is adapted to produce maximum amount of the first volatile compound even at the expense/with lower amount of the second volatile compound production during the first fermentation; and the fermentation unit is adapted to produce maximum amount of the second volatile compound from the biomass material that has been stripped off the first volatile compound during the pre-treatment stage in the first fermentation unit(s) and/or the pressure unit.

Biomasses and Fermentation

An anaerobic fermentation (or first or second fermentation) according to the invention can be conducted under thermophilic conditions and/or under mesophilic conditions. Accordingly, an anaerobic fermentation can be performed either by performing an anaerobic fermentation under thermophilic conditions, or under mesophilic conditions, or performing an anaerobic fermentation under thermophilic conditions followed by an anaerobic fermentation under mesophilic conditions, or by performing an anaerobic fermentation under mesophilic conditions followed by an anaerobic fermentation performed under thermophilic conditions.

Theromophilic conditions comprise temperatures ranging from 42° C. to 70° C., such as 45° C. to 60° C., preferably from 48° C. and 52° C. Mesophilic conditions comprise temperatures from 21° C. to 42° C., such as 21° C. to 25° C., for example 25° C. to 30° C., such as 30° C. to 35° C., for example 35° C. to 40° C., such as 40° C. to 42° C.

The thermophilic anaerobic fermentation and/or the mesophilic anaerobic fermentation is in one embodiment performed for about 5 to 15 days, such as 5 to 7 days, for example 7 to 10 days, such as 10 12 days, for example 12 to 15 days.

The pH for an anaerobic fermentation of a fermentable biomass material is in one embodiment in the range of from about 7 to 8.5, preferably between 7.4 and 8.4 and more preferably between 7.8 and 8.

Biomaterials according to the present invention in one embodiment comprise one or more carbon sources and one or more nitrogen sources. Carbon sources are typically polysaccharides or polymers which comprise polysaccharides. The polysaccharides are hydrolysed and/or oxidized into smaller constituents, such as e.g. oligosaccharides and/or monosaccharides. Exemplary polysaccharides are cellulose, hemicellulose, lignin and lignocellulose.

Fermentable biomass materials according to the present invention in one embodiment contain a maximum of 50% solid parts, such as a maximum of 40% solid parts, for example a maximum of 30% solid parts, such as a maximum of 20% solid parts by weight.

The fermentable biomass materials according to the present invention in one embodiment have a content of fibers of preferably more than 5% (w/w), for example more than 10% (w/w), such as more than 20% (w/w), and preferably less than 40% (w/w).

The biomass materials according to the invention is in one embodiment any organic waste biomass materials and in one embodiment selected from organic waste biomass materials and manures from domestic animals, including pigs, cattle, and domestic avian species.

In one embodiment, the fermentable biomass material is selected from the group consisting of biomasses comprising manures and slurries thereof, biomasses comprising crop residues, biomasses comprising silage crops, biomasses comprising animal carcasses and fractions thereof, slaughterhouse waste products, dairy waste products, meat and bone meal, and animal category 2 waste products, including any combination thereof, and/or the fermentable biomass material comprises one or more complex biomasses, and/or the fermentable biomass material comprises one or more complex biomasses each comprising a biomass material having a high percentage of organic Nitrogen, such as at least 5 kg, 6 kg, 7 kg, 8 kg, 10 kg, 15 kg, 20 kg, 25 kg or 30 kg of organic Nitrogen per ton of the biomass material, and/or the complex biomass comprises protein, oily substances and fats, and/or the complex biomass is selected from the group consisting of organic municipal waste, foodstuff waste, fermentable organic industrial waste products, fish waste products, slaughterhouse waste; deep litter or manure from animals, especially from cattle, pigs and poultry holdings; animal carcasses and/or fractions thereof, meat and bone meal, blood plasma and any produce originating from animals, straw, fibers and sawdust including any combination thereof, and/or In one embodiment the fermentable biomass material contains a maximum of 50% solid parts, such as a maximum of 40%, 30%, 20% or 10% solid parts, and/or the biomass material is in a fluid condition and comprises a maximum of 10% solid parts, and/or the biomass material is a liquid slurry obtained by the addition of water and/or water containing a low concentration of organic material, preferably less than 10% solid parts.

Fibrous Solid Fraction

In one embodiment of the invention the fermented biomass material (such as the first and/or second fermented biomass material) is fractionated into solid and liquid parts, thereby generating a fibrous solid fraction comprising solid and liquid parts and at least one liquid fraction. In one embodiment the fibrous solid fraction comprises one or more macromolecular constituents selected from the group consisting of cellulose, hemicellulose and lignin. The fractionation (or separation) in one embodiment is performed prior to being diverted to a fungal cultivation facility.

In one embodiment of the invention the fibrous solid fraction is subject to one or more additional treatments. The further steps are suitable for generating a final and ready-to-use fibrous solid substrate suitable for cultivating *Basidiomycete* cells, and having a reduced content of inorganic nitrogen compounds.

A sanitation treatment reduces or eliminates undesirable, viable microorganisms present in the fibrous solid fraction, and/or reduces the contents of undesirable, inorganic nitrogen-containing volatile compounds present in the fibrous solid fraction.

The sanitation treatment in one embodiment strips or removes by evaporation aqueous ammonia gas from the fibrous solid fraction. It follows that said stripping reduces the amount of nitrogen-containing volatile compounds and/or inorganic nitrogen precursor volatile compounds, such as ammonium and ammonium salts, in the fibrous solid fraction comprising organic and inorganic nitrogen parts.

In one embodiment of the present invention the fibrous solid fraction obtained from the degassed biomass material is subjected to a sanitation treatment, in one embodiment prior to cultivation of *Basidiomycete* species in said fibrous solid fraction.

In one embodiment a sanitation treatment comprises evaporating one or more volatile compounds under predetermined evaporation conditions characterized at least by heating the fibrous solid fraction to a temperature of at least 70° C. under alkaline pH conditions and at a pressure sufficient to evaporate said volatile compounds.

A sanitation treatment according to the invention in one embodiment comprises a) heating the fibrous solid fraction comprising organic and inorganic nitrogen parts to a temperature of more than 70° C., and optionally further comprises b) subjecting the fibrous solid fraction comprising organic and inorganic nitrogen parts to a pressure of more than 1 bar.

In one embodiment said fibrous solid fraction comprising organic and inorganic nitrogen parts is subjected to heating sufficient to evaporate volatile inorganic nitrogen compounds present in the fibrous solid fraction thus converting said inorganic nitrogen compounds to gaseous nitrogen containing volatile compounds, including ammonia.

The sanitation treatment in one embodiment comprises the step of heating the fibrous solid fraction comprising organic and inorganic nitrogen parts to a temperature of from 70° C. to 500° C., such as 70 to 80° C., for example 80 to 90° C., such as 90 to 100° C., for example 100 to 110° C., such as 110 to 120° C., for example 120 to 130° C., such as 130 to 140° C., for example 140 to 150° C., such as 150 to 160 ° C., for example 160 to 170° C., such as 170 to 180° C., for example 180 to 190° C., such as 190 to 200 ° C., for example 200 to 250 ° C., such as 250 to 300 ° C., for example 300 to 350 ° C., such as 350 to 400 ° C., for example 400 to 450 ° C., such as 450 to 500 ° C.

In one embodiment the heating of the fibrous solid fraction comprising organic and inorganic nitrogen parts to a temperature of from 70° C. to 500° C. results in the formation of an aqueous ammonia gas having a temperature of more than 70° C.

Independently of the above disclosed steps, the fibrous solid fraction comprising organic and inorganic nitrogen parts is in one embodiment subjected to a pressure of from 1 to 10 bar; such as 1 to 2 bar, for example 2 to 3 bar, such as 3 to 4 bar, for example 4 to 5 bar, such as 5 to 6 bar, for example 6 to 7 bar, such as 7 to 8 bar, for example 8 to 9 bar, such as 9 to 10 bar.

In one embodiment the fibrous solid fraction comprising organic and inorganic nitrogen parts is heated and dried, such as heated and dried in a dryer, such as a drum dryer.

In one embodiment the pH value of the fluid or liquid parts of said fibrous solid fraction is preferably above pH=7.5, for example above pH 8.0, such as above pH 8.5, at least during said sanitation treatment.

The fibrous solid fraction, after stripping of aqueous ammonia gas, preferably contains a reduced amount of inorganic nitrogen precursor volatile compounds, such as less than about 70% of the amount of inorganic nitrogen precursor volatile compounds present in the fibrous solid fraction comprising organic and inorganic nitrogen parts prior to stripping aqueous ammonia gas from the fibrous solid fraction; such as from about 20% to 25%, 25 to 30%, 30% to 40%, 40% to 50%, 50% to 55%, 55% to 60%, 60% to 65%, or 65 to 70% of the amount of said inorganic nitrogen precursor volatile compounds present in the fibrous solid fraction comprising organic and inorganic nitrogen parts prior to stripping aqueous ammonia gas from the fibrous solid fraction.

The inorganic nitrogen precursor volatile compounds in one embodiment comprise ammonium compounds capable of being converted into ammonia gas during said sanitation treatment.

The fibrous solid fraction is preferably suitable for cultivating *Basidiomycete* cells and capable of holding a desired content of water. The fibrous solid substrate in one embodiment of the invention comprises fibrous particles having an average particle size of more than 100 micron ($\mu$), such as more than 200 $\mu$, for example more than 300 $\mu$, such as more than 400 $\mu$, for example more than 500 $\mu$, such as more than 600 $\mu$, for example more than 700 $\mu$, such as more than 800 $\mu$, for example more than 900 $\mu$, such as more than 1000 $\mu$.

The fibrous solid substrate in one embodiment comprises fibrous particles having an average particle size of from 200 $\mu$ to 300 $\mu$, such as 300 to 400 $\mu$, for example 400 to 500 $\mu$, such as 500 to 600 $\mu$, for example 600 to 700 $\mu$, such as 700 to 800 $\mu$, for example 800 to 900 $\mu$, such as 900 to 1000 $\mu$, for example 1000 to 1200 $\mu$, such as 1250 to 1500 $\mu$, for example 1500 to 2000 $\mu$.

The fibrous solid substrate in one embodiment is able to hold a minimum content of water, calculated by mass, which is at least in the range of from about 10% to about 80%, such as 10% to 20%, for example 20% to 30%, such as 30% to 40%, for example 40% to 50%, such as 50% to 60%, for example 60% to 70%, such as 70% to 80%, In one embodiment the fibrous solid fraction is drained, separated and/or ammonia stripped.

In one embodiment the invention comprises a further step of draining liquid parts from the fibrous solid fraction comprising solid and liquid parts and obtaining a fibrous solid fraction comprising organic and inorganic nitrogen parts and having a total dry matter content of more than about 25% (w/w), such as more than 30% (w/w), for example more than 35% (w/w), and a residual liquid fraction.

In one embodiment the fibrous solid fraction is supplemented with one or more solid and/or liquid supplemental nutrient substrate compositions.

In order to obtain a "fluffy" consistency of the fibrous solid substrate suitable for cultivating *Basidiomycete* cells, the majority, and in some cases essentially all, inorganic solids present in the biomass material are separated from the fibrous solid fraction. The presence of inorganic solids in excessive and undesirable amounts will reduce the water holding capacity of the fibrous solid substrate.

The stripping of aqueous ammonia gas resulting in a reduction of the amount of inorganic nitrogen precursor volatile compounds present in the fibrous solid fraction generate an ammonia stripped, fibrous solid fraction comprising organic and inorganic nitrogen parts. In one embodiment fibrous solid fraction contains from about 0.5 kg to about 4.0 kg inorganic nitrogen ($NH_4$—N) per ton of fibrous solid fraction, such as 0.5 to 1.0 kg, for example 1.0 to 1.2 kg, such as 1.2 to 1.4 kg, for example 1.4 to 1.5 kg, such as 1.5 to 1.6 kg, for example 1.6 to 1.8 kg, such as 1.8 to 2 kg, for example 2 to 2.5 kg, such as 2.5 to 3 kg, for example 3 to 3.5 kg, such as 3.5 to 4 kg inorganic nitrogen ($NH_4$—N) per ton of fibrous solid fraction.

In one embodiment the ammonia stripped, fibrous solid fraction comprising organic and inorganic nitrogen parts contains from about 3 kg to about 30 kg organic nitrogen per ton of fibrous solid fraction, for example 3 to 5, such as 5 to 10, for example 10 to 11, such as 11 to 12, for example 12 to 13, such as 13 to 14, for example 14 to 15, such as 15 to 16, for example 16 to 17, such as 17 to 18, for example 18 to 19, such as 19 to 20, for example 20 to 25, such as 25 to 30 kg organic nitrogen per ton of fibrous solid fraction.

It may be desirable to adjust the pH of the fibrous solid substrate. The pH of the fibrous solid substrate is in one embodiment adjusted by adding substrate compositions to the fibrous solid fraction to obtain a fibrous solid substrate with liquid parts having, or being adjusted to have, a pH value of from 5.0 to 7.5

Once the nutrient composition of the fibrous solid substrate suitable for cultivating *Basidiomycete* cells has been controlled and a final, fibrous solid substrate has been manufactured, one can contact the fibrous solid substrate with one or more species of *Basidiomycete* cells, or spores, and cultivate said *Basidiomycete* cells, or spores, in said fibrous solid substrate.

By subjecting the biomass material to one or more separation steps resulting in the provision of a fibrous solid fraction comprising organic and inorganic nitrogen parts and at least one liquid fraction, and by evaporating from said fibrous solid fraction comprising organic and inorganic nitrogen parts an aqueous gas further comprising one or more volatile compounds, and obtaining a fibrous solid fraction comprising organic and inorganic nitrogen parts from which said one or more volatile compounds have been removed by evaporation, the present invention provides a method for controlling the composition of nutrients of a fibrous solid substrate suitable for cultivating *Basidiomycete* cells.

At least one of said one or more nutrients can be stripped as volatile compounds from said fibrous solid fraction by evaporation under predetermined conditions, wherein said one or more nutrients are converted into one or more volatile compounds which are stripped and removed from the composition of the final, fibrous solid substrate. The nutrient is in one embodiment evaporable or strippable inorganic nitrogen and/or sulphur containing nutrient compounds. Such compounds can be stripped as their gaseous counterparts, such as e.g. ammonia and hydrogen sulphide. Accordingly, the evaporable or strippable inorganic nitrogen and/or sulphur containing nutrient compounds can be considered precursor volatile compounds in this respect.

Evaporation of said one or more volatile compounds in one embodiment comprises a heating and drying treatment of the fibrous solid fraction comprising the steps of heating the fibrous solid fraction to a temperature of at least 70° C. under alkaline pH conditions, i.e. a pH above 7, such as above 7.5, for example a pH of above 8.0, and at a pressure sufficient to evaporate said volatile compounds.

Any of the above mentioned treatments including evaporation, stripping, separation and/or sanitation will serve to provide A) a fibrous solid fraction comprising organic and inorganic nitrogen parts and having i) an increased content (w/w) of organic nitrogen compounds, ii) a reduced content (w/w) of volatile compounds, or volatile precursor compound, and iii) a reduced content (w/w) of water, and B) an aqueous gas further comprising said one or more volatile compounds, including ammonia.

In one embodiment of the invention a volatile nitrogen-containing compounds is selected from the group consisting of gaseous ammonia, ammonia, inorganic nitrogen; an aqueous gas comprising ammonia; an aqueous gas comprising ammonia and volatile sulphur-containing compounds.

In one embodiment a volatile nitrogen-containing compounds further comprise volatile sulphur-containing compounds, including hydrogen sulphide.

In one embodiment of the invention a precursor volatile compound is selected from ammonium and ammonium salts.

In one embodiment of the invention a volatile methane-containing compound collectively form a gas comprising methane, such as a gas comprising more than 50% methane, such as more than 60% methane, such as more than 70% methane, such as more than 80% methane, such as more than 90% methane, such as more than 95% methane, or such as more than 99% methane, such as a biogas.

Additional Method Steps

The methods of the present invention in one embodiment comprise a pre-treatment anaerobic fermentation step followed be either a) a pressure cooking step and an ammonia stripping step, which steps are performed prior to at least one subsequent anaerobic fermentation step for biogas generation at the fermentation facility, or b) an ammonia stripping step performed prior to the at least one subsequent anaerobic fermentation step.

The pre-treatment fermentation step preferably results in the production of ammonia that is collected and thus not diverted to a further biogas fermenter where the production of predominantly biogas in the further fermentation step takes place.

Preferably, the pre-treatment fermentation step according to the first aspect of the present invention is performed in combination with an ammonia stripping and/or an ammonia collection step. By initially removing ammonia in a pre-treatment fermentation step it is possible to increase the production of biogas in a further fermentation step in a second fermentation facility. In one embodiment, the initial pre-treatment fermentation step does not involve thermophilic fermentation.

Thus, according to one embodiment of the present invention there is provided a method for producing first volatile nitrogen-containing compounds collectively forming gaseous ammonia and second volatile methane-containing compounds collectively forming a biogas through sequential fermentations of a biomass material comprising solid and/or liquid parts In one embodiment the methods of the invention further comprises subjecting the biomass material, such as an at least partly degassed biomass material, to one or more separation steps resulting in the provision of a) a fibrous solid fraction comprising organic and inorganic nitrogen parts and b) at least one liquid fraction comprising solid and liquid organic and inorganic phosphor-containing parts.

In one embodiment the methods of the invention further comprises separating solid and liquid parts of the at least one liquid fraction comprising solid and liquid organic and inorganic phosphor-containing parts by fractionation and/or sedimentation, and obtaining a) a fibrous solid fraction, b) a first solid, phosphor-containing fraction or sediment suitable for being used as, or added to, a phosphor-containing agricultural fertilizer, and c) a first liquid permeate fraction comprising solid and/or liquid nitrogen-and/or phosphor-containing parts.

In one embodiment of the invention the first solid, phosphor-containing fraction or sediment and the first liquid permeate fraction of the invention is obtained by passing the biomass material comprising solid and liquid parts over a first sieve membrane allowing the first solid, phosphor-containing fraction, or sediment, and the first liquid permeate fraction to pass through the membrane, while the fibrous solid fraction is retained, and thereby separated from the first solid, phosphor-containing fraction, or sediment, and the first liquid permeate fraction.

In one embodiment the methods of the invention comprise the further step of draining liquid parts from the fibrous solid fraction comprising solid and liquid parts and obtaining a residual liquid fraction.

In one embodiment the methods of the invention comprise the further step of combining the residual liquid fraction and the first liquid permeate fraction into a combined liquid fraction comprising solid and liquid parts, and subjecting said combined liquid fraction comprising solid and liquid parts to further separation of solid and liquid parts contained therein.

The combined liquid fraction comprising solid and liquid parts is in one embodiment passed over a second or further sieve membrane having a smaller pore size than the first sieve membrane, and the combined liquid fraction comprising solid and liquid parts separated into:

a) a second solid, phosphor-containing fraction or sediment,
b) a second liquid permeate fraction, and
c) a solid fraction concentrate comprising solid and liquid parts.

In one embodiment the separation comprises diverting the combined liquid fraction comprising solid and liquid parts over or through the second or further sieve membrane, retaining the solid fraction concentrate comprising solid and liquid parts and separating said solid fraction concentrate from the second solid, phosphor-comprising fraction or sediment, and the second liquid permeate fraction.

In a still further step, the said first and second solid, phosphor-containing fractions or sediments are dried.

In one embodiment the gaseous ammonia generated during the initial, anaerobic fermentation is stripped from the partly degassed biomass material by heating the partly degassed biomass material in a designated stripper and sanitation tank to a temperature of at least about 70° C. at a pressure sufficient to strip said volatile compounds, and collecting and/or storing the stripped, gaseous ammonia, preferably storing the stripped ammonia by converting the ammonia gas to a solid ammonium salt compound by a reaction with a suitable acid.

In one embodiment the temperature in the stripper and sanitation tank is 75° C. to 95° C., such as 78° C. to 90° C., such as to 80° C. to 88° C., such as 82° C. to 85° C.

In one embodiment the pH in the stripper and sanitation tank is maintained from 9 to 12, such as 9.5 to 11.8, such as 10 to 11.3, such as 10.5 to 11. In one embodiment the pH is controlled by addition of lime to the stripper and sanitation tank.

In one embodiment said sanitation treatment that reduces the contents of volatile nitrogen-containing compounds and/or precursor volatile compounds present in the fibrous solid fraction, produces and/or evaporates volatile nitrogen-containing compounds and/or precursor volatile compounds.

In one embodiment said volatile nitrogen-containing compounds and/or precursor volatile compounds are diverted to and/or collected in a stripper and sanitation tank.

In one embodiment said volatile nitrogen-containing compounds comprise gaseous ammonia which ammonia gas is converted to a solid ammonium salt compound by reaction with an acid, such as an inorganic or organic acid.

The stripped ammonia gas can be converted go a solid ammonium salt compound by a reaction with an acid.

In one embodiment the solid ammonium salt compound is stored. In one embodiment the solid ammonium salt compound is used to enrich a composition, such as an agricultural fertilizer.

According to the invention any stripped ammonia gas is in one embodiment collected and/or converted into a solid ammonium compound fraction comprising one or more inorganic, ammonium salt compounds, such as for example ammonium sulphate, following a reaction with an acid, such as for example sulphuric acid, or any other, suitable inorganic or organic acid.

In one embodiment the methods according to the invention further comprise one or more of the steps of
i) heating the fibrous solid fraction to a temperature of more than 70° C., wherein said heating results in the formation of an aqueous ammonia gas having a temperature of more than 70° C., and/or
ii) stripping said aqueous ammonia gas having a temperature of more than 70° C. from the drained, fibrous solid fraction, and/or
iii) diverting the aqueous ammonia gas having a temperature of more than 70° C. to the stripper and sanitation tank, and/or
iv) using the aqueous ammonia gas having a temperature of more than 70° C. for heating the partly degassed biomass material present in the stripper and sanitation tank, and/or
v) optionally heating the partly degassed biomass material present in the stripper and sanitation tank by one or more additional heating sources.

In one embodiment the sanitation treatment exploits primary and secondary combustion air sources, including exhaust air sources, present in or generated in the biogas fermentation facility as a result of performing said sanitation, wherein said primary and secondary combustion air sources are diverted to a stripper and sanitation tank for conversion and/or collection as solids.

In one embodiment the exploitation of primary combustion air sources from the biogas fermentation facility results in generating a negative pressure in the biogas fermentation facility space, which negative pressure prevents or contributes to preventing any undesirable odorants from escaping the biogas fermentation facility, wherein said odorants comprise one or more volatile nitrogen-containing compounds and/or volatile sulphur-containing compounds.

In one embodiment the (first) biomass material suitable for anaerobic fermentation and biogas production is a partly degassed biomass material obtained by performing an initial, anaerobic fermentation resulting in the production of a gaseous fraction comprising ammonia and biogas.

In one embodiment of the present invention, the first biomass material suitable for anaerobic fermentation and biogas production is a partly degassed biomass material obtained by performing an initial, anaerobic batch fermentation resulting in the production of a gaseous fraction comprising ammonia and biogas.

In one embodiment the continuous, anaerobic biogas fermentation generates a fermented, degassed biomass material suitable for use as a substrate for cultivating one or more fungal species, and the fermented, degassed biomass material obtained from the continuous, anaerobic biogas fermentation and the anaerobic batch fermented biomass material obtained from the batch fermentation are combined and used as a substrate for cultivation of one or more fungal species.

The further biomass materials according to the invention is in one embodiment any organic waste biomass materials and in one embodiment selected from organic waste biomass materials and manures from domestic animals, including pigs, cattle, and domestic avian species.

*Basidiomycete*

*Basidiomycete*, *Basidiomycetes* and *Basidiomycete* cells and/or spores are used interchangeably herein.

Many fungal organisms including the *Basidiomycetes* produce and secrete extracellular enzymes capable of degrading or digesting the macromolecular nutrient constituents comprised in the fibrous solid substrate, including cellulose, hemicellulose, lignin and lignocellulose.

Hence, by performing, sequentially in any order, anaerobic biogas fermentations and *Basidiomycete* cultivation methods using a fibrous solid fraction from the spent biomass as a substrate for the cultivation of *Basidiomycetes* the macromolecular nutrient constituents present in a biomass material can be more efficiently utilized.

The digestion by extracellular *Basidiomycete* enzymes of said macromolecular nutrient constituents results in a hydrolysis and/or an oxidation of at least part of said macromolecular constituents In one embodiment said hydrolysis and/or oxidation of at least part of said macromolecular constituents generates a spent fungal substrate capable of being fermented by microbial organisms involved in one or more stages of a biogas fermentation. In one embodiment said microbial organisms involved in said one or more stages of a biogas fermentation metabolises the hydrolysis and/or oxidation products resulting from the hydrolysis and/or oxidation of said macromolecular constituents.

Suitable fungal organisms according to the invention comprise organisms constituting the phylum Basidiomycota of the kingdom Fungi, or, in older classification schemes, the class *Basidiomycetes* of the kingdom Plantae, i.e. fungal organisms characterized by bearing the spores on a basidium, including edible mushrooms.

In one embodiment the *Basidiomycetes* are selected from the group of *Basidiomycetes* belonging to any of the subclasses of Agaricomycetidae, Exobasidiomycetidae, Tremellomycetidae and Ustilaginomycetidae, wherein said *Basidiomycete* is able to degrade or digest macromolecular nutrient constituents including cellulose, hemicellulose, lignin, and lignocellulose.

Preferred *Basidiomycete* cells are those which are edible, in one embodiment including a fungus or fungal cell selected from the genera of *Agaricus, Lentinula* (*Lentinus*), *Flammulina, Pleurotus*; and *Lyophyllum*. In one embodiment the *Basidiomycete* cell is selected from the species of *Lentinula* (*Lentinus*) *edodes* (shiitake); edible *Agaricus* species (e.g. *Agaricus bisporus, Agaricus campestris, Agaricus subrufescens*), *Flammulina velutipes* (Enokitake), *Pleurotus eryngii* (*Eryngii*), *Pleurotus ostreatus*; and *Shimeji* (e.g. *Lyophyllum shimejl, Buna-shimeji, Bunapi-shimeji, Hatake-shimeji, shirotamogidake, velvet pioppino*).

The cultivation of the *Basidiomycete* cell in one embodiment takes place at a temperature of from 15° C. to 35° C., for example 15° C. to 17° C., such as 17° C. to 20° C., for example 20° C. to 22° C., such as 22° C. to 25° C., for example 25° C. to 30° C., such as 30° C. to 35° C. The cultivation of the *Basidiomycete* cell in one embodiment takes place in a fibrous solid substrate having a moisture content of from 50% by mass to 70% by mass, such as a moisture content of about 60% by mass.

Conventional fungal cultivation protocols can be followed as long as the substrate for the cultivation is a fibrous solid substrate isolated from a spent, at least partly degassed biomass material following anaerobic biogas fermentation.

Macromolecular Nutrient Constituents

The fibrous solid substrate suitable for cultivating *Basidiomycete* cells in a preferred embodiment comprises one or more macromolecular nutrient constituents selected from the group consisting of cellulose, hemicellulose lignin and lignocellulose. The fibrous solid substrate in one embodiment comprises more than one macromolecular constituent, such as two or three macromolecular constituents selected from the group consisting of cellulose, hemicellulose and lignin.

The macromolecular nutrient constituents are difficult for the microbial organisms such as anaerobic bacteria involved in one or more stages of an anaerobic fermentation and biogas production to digest.

Lignocellulose in the form of a feed stock biomass material comprises cellulose, hemicellulose and lignin as macromolecular constituents and lignocellulose or lignocellulose-containing material is an example of a biomass material used for biogas production.

The early stages of a biogas fermentation includes an initial stage of hydrolysis of macromolecular nutrient constituents into their basic constituents, or into nutrient constituents which can more readily be metabolized and fermented by the microbial organisms involved in one or more stages of an anaerobic fermentation and biogas production. Metabolism of nutrient constituents is essential for the production of biogas as no fermentable and energy generating microbial activities can be carried out in the absence of such metabolism.

It is a particular challenge during an anaerobic biogas fermentation that no, or an insufficient hydrolysis takes place of macromolecular nutrient constituents into their basic constituents, or into nutrient constituents which can more readily be metabolized and fermented by the microbial organisms involved in one or more stages of an anaerobic fermentation and biogas production. Accordingly, the fibrous solid substrate according to the present invention comprises one or more macromolecular nutrient constituents which are difficult, if not impossible, for many microbial organisms involved in one or more stages of an anaerobic fermentation and biogas production to digest.

The general lack of hydrolysis of said macromolecular constituents, including cellulose, hemicellulose and lignin, by methanogenic and other anaerobic bacteria involved in the production of biogas under anaerobic fermentation conditions, will result in said macromolecular constituents being present during an anaerobic biogas fermentation during one or more stages of the anaerobic biogas fermentation, including the stages selected from acidogenesis, acetogenesis and methanogenesis.

In one embodiment the fibrous solid substrate suitable for cultivating fungal such as *Basidiomycete* cells comprising one or more macromolecular nutrient constituents selected from the group consisting of cellulose, hemicellulose lignin and lignocellulose are at least partly digested by the cultivation of fungal cells, leaving a spent fungal substrate which, optionally supplemented with further biomass, can be used as a feed stock for a new round of anaerobic fermentation and biogas production.

Methods for Pre-Treatment of Biomass Materials Prior to Anaerobic Fermentation

The above-cited macromolecular constituents can be degraded enzymatically as well as by mechanical and/or chemical treatments of biomass materials containing such macromolecular constituents prior to anaerobic fermentation thereof.

In one embodiment a biomass material according to the present invention is subjected to one or more pre-treatment processing steps in any suitable way or combination prior to performing an anaerobic fermentation on the pre-treated biomass material.

The pre-treatment is in one embodiment carried out before enzymatic hydrolysis and/or oxidation of the biomaterial components forming part of the biomaterial, and in another embodiment at the same time as an enzymatic hydrolysis and/or oxidation takes place.

The enzymatic hydrolysis and/or oxidation is in one embodiment catalyzed by endogeneous microbial organisms present in the biomaterial to be subjected to anaerobic fermentation. In another embodiment the enzymes are exogeneously added, for example as bulk enzymes produced by a producer of industrial enzymes. In one embodiment the microbial organism is *Basidiomycetes*.

A pre-treatment according to the invention in one embodiment reduce the size of the solids and macromolecular constituents making up the biomass material. The pre-treatment thus increase or supplement the rate of hydrolysis of the biomass materials prior to—or during—anaerobic biogas fermentation. A pre-treatment according to the invention in one embodiment promotes the separation and/or release of cellulose, hemicellulose and/or lignin.

Pre-treatment processes, such as wet-oxidation, steam explosion and alkaline pre-treatment steps, will preferably target lignin, while dilute acid and auto-hydrolysis will preferably target hemicellulose containing materials.

The pre-treatment step is in one embodiment a conventional pre-treatment step using techniques well known in the art. In one embodiment pre-treatment takes place in a slurry of lignocellulose-containing material and water. The lignocellulose-containing material during pre-treatment is in one embodiment present in an amount between 10-80 wt.-%, such as 10-20 wt.-%, for example 20-30 wt.-%, such as 30-40 wt.-%, for example 40-50 wt.-%, such as 50-60 wt.-%, for example 60-70 wt.-%, such as 70-80 wt.-%, such as around 50 wt-%.

The biomass material or lignocellulose-containing material according to the invention is in one embodiment chemically, mechanically and/or biologically pre-treated before, before and during, or during, hydrolysis or fermentation. Mechanical pre-treatment may be carried out alone or combined with chemical or biological pre-treatment processes The pre-treated biomass material preferably has a neutral to basic pH value before anaerobic fermentation/when it is added to the biogas digester. An acidic biomass may slow down or complicate the biogas conversion process due to inhibition of methanogenic microorganisms. The pH-value of the biomass entering the anaerobic digester is preferably between 7 and 10, such as from 7.2 to 10; for example from 7.4 to 10, such as from 7.6 to 10, for example from 7.8 to 10, such as from about 8 to 10, for example around pH 8.5. The pH may be adjusted using NaOH, $Na_2CO_3$, $NaHCO_3$, $Ca(OH)_2$, CaO lime hydrate, ammonia and/or KOH or the like.

In one embodiment the pre-treatment includes subjecting a biomass material to thermo-chemical treatment in a lime pressure cooker. The pressure cooking pre-treatment breaks down complex macromolecular structures of the biomass material and also contributes to and results in stripping of ammonia from the biomass.

In another embodiment, instead of or in addition to a thermo-chemical pre-treatment step, the biomass material can be subjected to a pre-fermentation in the pre-fermenters with N-stripping.

Chemical Pre-Treatment

In one embodiment a biomass material according to the present invention is subjected to one or more chemical pre-treatment steps.

A chemical pre-treatment include treatment with; for example, dilute acid, lime, lime hydrate, alkaline, NaOH, Na$_2$CO$_3$, NaHCO$_3$, Ca(OH)$_2$, organic solvent, cellulose solvent, ammonia, KOH, sulfur dioxide, carbon dioxide, enzymatic hydrolysis. Pre-treatment processes using ammonia are described in, e.g., WO 2006/110891, WO 2006/11899, WO 2006/11900, WO 2006/110901.

Further, wet oxidation and pH-controlled hydro-thermolysis are also considered chemical pre-treatment. Wet oxidation techniques involve use of oxidizing agents, such as: sulphite based oxidizing agents or the like. Examples of solvent pre-treatments include treatment with DMSO (Dimethyl Sulfoxide) or the like. Other examples of suitable pre-treatment processes are described by Schell et al. (2003) Appl. Biochem and Biotechn. Vol. 105-108, p. 69-85, and Mosier et al. Bioresource Technology 96 (2005) 673-686, and US publication no. 2002/0164730.

Mechanical Pre-Treatment

In one embodiment a biomass material according to the present invention is subjected to one or more mechanical pre-treatment steps, or homogenization.

The term "mechanical pre-treatment" refers to any mechanical (or physical) pre-treatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the size). Comminution includes dry milling, wet milling, vibratory ball milling and grinding. Mechanical pre- treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pre- treatment is carried out as a batch-process, in a steam gun hydrolyzer system which uses high pressure and high temperature as defined above. A Sunds Hydrolyzer (available from Sunds Defibrator AB (Sweden) may be used.

In one embodiment the lignocellulose-containing material is subjected to a irradiation pre-treatment. The term "irradiation pre-treatment" refers to any pre- treatment by microwave e.g. as described by Zhu et al. "Production of ethanol from microwave-assisted alkali pre-treated wheat straw" in Process Biochemistry 41 (2006) 869-873 or ultrasonic pre-treatment, e.g., as described by e.g. Li et al. "A kinetic study on enzymatic hydrolysis of a variety of pulps for its enhancement with continuous ultrasonic irradiation", in Biochemical Engineering Journal 19 (2004) 155-164.

In one embodiment the lignocellulose-containing material is subjected to both chemical and mechanical pre-treatment. For instance, the pre-treatment step may involve dilute or mild acid treatment and high temperature and/or pressure treatment. The chemical and mechanical pre-treatments may be carried out sequentially or simultaneously, as desired.

In an embodiment the pre-treatment is carried out as a dilute and/or mild acid steam explosion step. In another preferred embodiment pre-treatment is carried out as an ammonia fiber explosion (or AFEX pre-treatment step).

In yet another embodiment, a base is added to the lignocellulose-containing material or the slurry prior to or while it is being homogenized; preferably the base is NaOH, Na$_2$CO$_3$, NaHCO$_3$, Ca(OH)$_2$, lime hydrate, ammonia and/or KOH or the like.

Biological Pre-Treatment

In one embodiment a biomass material according to the present invention is subjected to one or more biological pre-treatment steps. The term "biological pre-treatment" refers to any biological pre-treatment which promotes the separation and/or release of cellulose, hemicellulose, and/or lignin from the lignocellulose-containing material.

In one embodiment the biological pre-treatment technique involve applying lignin-solubilizing microorganisms.

Enzymatic Pre-Treatment

In one embodiment a biomass material according to the present invention is subjected to one or more enzymatic pre-treatment steps. Before the pre-treated lignocellulose-containing material is fermented it can preferably be hydrolyzed enzymatically to break down especially hemicellulose and/or cellulose into fermentable sugars.

According to the invention enzymatic hydrolysis is performed in several steps. The lignocellulose-containing material to be hydrolyzed in one embodiment constitutes above 2.5% wt-% DS (dry solids), preferably above 5% wt-% DS, preferably above 10% wt-% DS, preferably above 15 wt-% DS, preferably above 20 wt.-% DS, more preferably above 25 wt-% DS of the slurry of step a).

In one embodiment the lignocellulose-containing material is subjected to the action of one or more enzyme activities of enzymes selected from the group consisting of an amylolytic enzyme (amylase), a lipolytic enzyme (lipase), a proteolytic enzyme (protease), a hemicellulase, a pectinolytic enzyme (pectinase), a cellulolytic enzyme (cellulase), an oxidoreductase and a plant cell-wall degrading enzyme.

In one embodiment, the one or more enzyme for enzymatic pre-treatment is selected from the group consisting of aminopeptidase, alpha-amylase, amyloglucosidase, arabinofuranosidase, arabinoxylanase, beta-glucanase, carbohydrase, carboxypeptidase, catalase, cellobiohydrolase, cellulase, chitinase, cutinase, cyclodextrin glycosyltransferase, ferulic acid esterase, deoxyribonuclease, endo-cellulase, endo-glucanase, endo-xylanase, esterase, galactosidase, beta-galactosidase, glucoamylase, glucose oxidase, glucosidase, haloperoxidase, hemicellulase, invertase, isomerase, laccase, ligase, lipase, lyase, mannanase, mannase, mannosidase, oxidase, pectate lyase, pectin lyase, pectin trans-eliminase, pectin ethylesterase, pectin methylesterase, pectinolytic enzyme, peroxidase, protease, phytase, phenoloxidase, polygalacturonase, polyphenoloxidase, proteolytic enzyme, rhamnogalacturonan lyase, rhamnoglucanase rhamnogalacturonase, ribonuclease, SPS-ase, transferase, transglutaminase, xylanase and xyloglucanase.

The enzymatic activities listed is in one embodiment provided by *Basidiomycete* cells producing extracellular enzymes having said activates, or in another embodiment by other microbial organisms. In yet another embodiment endogenic enzymes are provided e.g. in a bulk enzyme preparation e.g. to a biomass material prior to anaerobic biogas fermentation.

Hydrolytic enzymes, proteases and oxidases produced by *Basidiomycetes* and other fungal species are preferred as these are present in the spent mushroom substrate which constitutes an input biomaterial for pre-treated and anaerobic fermentation.

EXAMPLES

Table 1 shows the characteristics for types of waste products and biomasses suitable for production of mushroom substrate and the possible conversion of organic N to ammonia N if used as single biomass as feed stock for biogas.

Type of Waste for Substrate & Biogas N-Contents and Possible Levels of Conversion of Organic N to Ammonia N

TABLE 1

| Type of special waste and/or mix | Dry matter | Content in feed stock N Total | N org | NH4+ | Max N org conv 70% | "Meso" Mother 3.8 | Conversion of N org of N org Total input | M-Meso+ Pre-dig 5.8 | of N org Total input | Term/ meso 3.5 | of N org Total input |
|---|---|---|---|---|---|---|---|---|---|---|---|
| Spent substrate | 33.0% | 7.0 | 5.6 | 1.4 | 3.9 | 2.4 | 43% | 3.9 | 70% | 2.1 | 38% |
| Solid manure egglayers | 40.0% | 18.9 | 12.3 | 6.6 | 8.6 | 0.0 | 0% | 0.0 | 0% | 0.0 | 0% |
| Solid manure chickens | 48.0% | 21.9 | 15.3 | 6.6 | 10.7 | 0.0 | 0% | 0.0 | 0% | 0.0 | 0% |
| Deep littter - cattle | 30.0% | 9.5 | 6.6 | 2.9 | 4.6 | 0.9 | 14% | 2.9 | 44% | 0.6 | 9% |
| Liquid manure - cattle | 8.5% | 5.5 | 2.2 | 3.3 | 1.5 | 0.5 | 23% | 1.5 | 70% | 0.2 | 9% |
| Fruits & vegetables refuse | 20.0% | 6.0 | 4.2 | 1.8 | 2.9 | 2.0 | 48% | 2.9 | 70% | 1.7 | 40% |
| N-stripped biomass | 17.5% | 2.6 | 2.0 | 0.6 | 1.4 | 1.4 | 70% | 1.4 | 70% | 1.4 | 70% |
| N-stripped concentrate | 14.9% | 3.0 | 0.6 | 2.4 | 0.4 | 0.4 | 70% | 0.4 | 70% | 0.4 | 70% |
| N-stripped permeate | 2.9% | 1.0 | 0.3 | 0.7 | 0.2 | 0.2 | 70% | 0.2 | 70% | 0.2 | 70% |
| N-Water | 0.0% | 0.1 | 0.0 | 0.1 | 0.0 | 0.0 | 70% | 0.0 | 70% | 0.0 | 70% |

Use of spent substrate in feed stocks for biogas is illustrated in tables 2, 3 and 4.

Example 1

Spent Substrate+Manure Egglayers & Chicken&Cattle+N-Stripped Biomass+N-Water

TABLE 2

| Type of special waste and/or mix | Mix % of total | Content in feed stock Dry matter % | N Total kg/ton | N org kg/ton | NH4+ kg/ton | Acc N org conv | "Meso" Mother 3.8 | Conversion of N org of N org Total input | Pre-digesters 5.8 | of N org Total input | Termo/ meso 3.5 | of N org Total input |
|---|---|---|---|---|---|---|---|---|---|---|---|---|
| N-stripping effect | | | | | 90% | 70% | | | | | | |
| Spent substrate | 30% | 33.0% | 7.0 | 5.6 | 1.4 | | | | | | | |
| Solid manure egglayers | 5% | 40.0% | 18.9 | 12.3 | 6.6 | | | | | | | |
| Solid manure chickens | 5% | 48.0% | 21.9 | 15.3 | 6.6 | | | | | | | |
| Deep littter - cattle | 5% | 30.0% | 9.5 | 6.6 | 2.9 | | | | | | | |
| Liquid manure - cattle | 25% | 8.5% | 5.5 | 2.2 | 3.3 | | | | | | | |
| Fruits & vegetables refuse | 0% | 0.0% | 0.0 | 0.0 | 0.0 | | | | | | | |
| N-stripped biomass | 0% | 0.0% | 0.0 | 0.0 | 0.0 | | | | | | | |
| N-stripped concentrate | 0% | 0.0% | 0.0 | 0.0 | 0.0 | | | | | | | |
| N-stripped permeate | 4% | 2.9% | 1.0 | 0.3 | 0.7 | | | | | | | |
| N-water | 26% | 0.0% | 0.1 | 0.0 | 0.1 | | | | | | | |
| Bio Mix | 100% | 18.0% | 6.1 | 4.0 | 2.1 | | | | | | | |
| Mix in total | 100% | 18.0% | 6.1 | 4.0 | 2.1 | 2.8 | | | | | 1.4 | 35% |
| after M-meso | | | 6.1 | 2.3 | 3.8 | 2.8 | 1.7 | 43% | | | | |
| after Pre-digesters | | | 6.1 | 1.2 | 4.9 | 1.1 | | | 1.1 | 70% | | |
| after N-stripping | | | 1.7 | 1.2 | 0.5 | | | | | | | |

Example 2

Spent Substrate+Manure Egglayers & Cattle+N-Stripped Biomass+N-Water

TABLE 3

| Type of special waste and/or mix | Mix % of total | Content in feed stock Dry matter % | N Total kg/ton | N org kg/ton | NH4+ kg/ton | Acc N org conv | "Meso" Mother 3.8 | Conversion of N org of N org Total input | Pre-digesters 5.8 | of N org Total input | Termo/ meso 3.5 | of N org Total input |
|---|---|---|---|---|---|---|---|---|---|---|---|---|
| N-stripping effect | | | | | 90% | 0% | | | | | | |
| Spent substrate | 30% | 33.0% | 7.0 | 5.6 | 1.4 | | | | | | | |
| Solid manure egglayers | 10% | 40.0% | 18.9 | 12.3 | 6.6 | | | | | | | |
| Solid manure chickens | 0% | 0.0% | 0.0 | 0.0 | 0.0 | | | | | | | |
| Deep littter - cattle | 5% | 30.0% | 9.5 | 6.6 | 2.9 | | | | | | | |

TABLE 3-continued

| Type of special waste and/or mix | Mix % of total | Dry matter % | N Total kg/ton | N org kg/ton | NH4+ kg/ton | Acc N org conv | "Meso" Mother 3.8 | of N org Total input | Pre-digesters 5.8 | of N org Total input | Termo/meso 3.5 | of N org Total input |
|---|---|---|---|---|---|---|---|---|---|---|---|---|
| Liquid manure - cattle | 25% | 8.5% | 5.5 | 2.2 | 3.3 | | | | | | | |
| Fruits & vegetables refuse | 0% | 0.0% | 0.0 | 0.0 | 0.0 | | | | | | | |
| N-stripped biomass | 0% | 0.0% | 0.0 | 0.0 | 0.0 | | | | | | | |
| N-stripped concentrate | 0% | 0.0% | 0.0 | 0.0 | 0.0 | | | | | | | |
| N-stripped permeate | 15% | 2.9% | 1.0 | 0.3 | 0.7 | | | | | | | |
| N-water | 15% | 0.0% | 0.1 | 0.0 | 0.1 | | | | | | | |
| Bio Mix | 100% | 18.0% | 6.0 | 3.8 | 2.2 | | | | | | | |
| Mix in total | 100% | 18.0% | 6.0 | 3.8 | 2.2 | 2.7 | | | | | 1.3 | 35% |
| after M-meso | | | 6.0 | 2.2 | 3.8 | 2.7 | 1.6 | 43% | | | | |
| after Pre-digesters | | | 6.0 | 1.2 | 4.9 | 1.1 | | | 1.1 | 70% | | |
| after N-stripping | | | 1.6 | 1.2 | 0.5 | | | | | | | |

Example 3

Spent Substrate+Manure Egglayers+Fruits&Vegetable Refuse+N-Stripped Biomass+N-Water The data in Table 5 are based on a specific mix of biomass and interaction between a "mushroom substrate" production unit with Meso Mother reactor, pre-reactors, dryer, N-strippers and N-absorber facilities and a conventional termo/meso biogas plant with Sep & Sed facilities as add on.

TABLE 4

| Type of special waste and/or mix | Mix % of total | Dry matter % | N Total kg/ton | N org kg/ton | NH4+ kg/ton | Acc N org conv | "Meso" Mother 3.8 | of N org Total input | Pre-digesters 5.8 | of N org Total input | Termo/meso 3.5 | of N org Total input |
|---|---|---|---|---|---|---|---|---|---|---|---|---|
| N-stripping effect | | | | | 90% | 0% | | | | | | |
| Spent substrate | 30% | 33.0% | 7.0 | 5.6 | 1.4 | | | | | | | |
| Solid manure egglayers | 12% | 40.0% | 18.9 | 12.3 | 6.6 | | | | | | | |
| Solid manure chickens | 0% | 0.0% | 0.0 | 0.0 | 0.0 | | | | | | | |
| Deep littter - cattle | 0% | 0.0% | 0.0 | 0.0 | 0.0 | | | | | | | |
| Liquid manure - cattle | 0% | 0.0% | 0.0 | 0.0 | 0.0 | | | | | | | |
| Fruits & vegetables refuse | 15% | 20.0% | 6.0 | 4.2 | 1.8 | | | | | | | |
| N-stripped biomass | 0% | 0.0% | 0.0 | 0.0 | 0.0 | | | | | | | |
| N-stripped concentrate | 0% | 0.0% | 0.0 | 0.0 | 0.0 | | | | | | | |
| N-stripped permeate | 10% | 2.9% | 1.0 | 0.3 | 0.7 | | | | | | | |
| N-water | 33% | 0.0% | 0.1 | 0.0 | 0.1 | | | | | | | |
| Bio Mix | 100% | 18.0% | 5.4 | 3.8 | 1.6 | | | | | | | |
| Mix in total | 100% | 18.0% | 5.4 | 3.8 | 1.6 | 2.7 | | | | | 1.9 | 50% |
| after M-meso | | | 5.4 | 1.6 | 3.8 | 2.7 | 2.2 | 58% | | | | |
| after Pre-digesters | | | 5.4 | 1.1 | 4.3 | 0.5 | | | 0.5 | 70% | | |
| after N-stripping | | | 1.6 | 1.1 | 0.4 | | | | | | | |

In Examples 1 and 2 the advantages linked to the present invention are clearly visible. Without recycling of N-stripped permeate and dilution with N-water from N-absorption, the feed stock mix will have an inhibitory level of $NH_4^+$-N before entering the anaerobic digesters. In the absence of N stripping, one would have to mix organic materials high in N with organic materials low in N—i.e. add high N containing organic materials in small portions to a mixture of organic materials to be fermented.

The anaerobic fermentation resulting in the production of biogas is followed by one or more processing steps aimed to strip ammonia N from the organic material after to the biogas production from pre-digestion in fermentation facilities, heating and drying.

The termo/meso biogas plant is supplying fiber from separation to the "mushroom substrate" production unit and gets in return N-stripped pre-digested biomass and N-stripped concentrate—both pre-heated—as new feed stock. The main scope is to produce basic substrate for mushroom production according to FIG. 8 and adjust moisture content by adding N-water and specific types of supplementary fibers.

Based on the findings in Table 5 the share of basic substrate will depend on desired content moisture and composition of nutrients in the final substrate.

TABLE 5

BioEnergy & New Food - Alternative 1

| Pre-digested | Ton | DM ton | DM % | VS ton | VS % of DM | NH4+ kg/ton | Norg kg/ton |
|---|---|---|---|---|---|---|---|
| Basis feed stock | 33000 | 6620 | 20.1% | 5045 | 76% | 4.50 | 5.93 |
| Spent mushroom substrate | 15000 | 5700 | 38.0% | 3990 | 70% | 1.20 | 4.80 |
| N-striped biomass | 13000 | 2319 | 17.8% | 1396 | 60% | 0.60 | 2.02 |
| N-striped concentrate | 0 | 0 | 0.0% | 0 | 0% | 0.00 | 0.00 |
| N-striped permeate | 14703 | 422 | 2.9% | 190 | 45% | 0.71 | 0.32 |
| N-water from drying | 7062 | 35 | 0.5% | 24 | 68% | 2.70 | 0.03 |
| Total input | 82765 | 15096 | 18.2% | 10645 | 71% | 2.46 | 3.61 |
| Degasified | 79229 | 11561 | 14.6% | 7108 | 61% | 4.66 | 1.69 |
| Degasified for N-striping | 34229 | 4994 | 14.6% | 3071 | 61% | 4.66 | 1.69 |
| Fiber from separation | 8630 | 3020 | 35% | 2296 | 76% | 3.54 | 4.04 |
| Concentrate from sep | 12585 | 1510 | 12.0% | 1148 | 76% | 4.80 | 1.39 |
| P-sed from sep | 5472 | 1642 | 30.0% | 410 | 25% | 3.82 | 3.47 |
| Permeate from sep | 18314 | 394 | 2.2% | 183 | 47% | 5.34 | 0.25 |
| Total out from sep | 45000 | 6566 | 14.6% | 4037 | 61% | 4.66 | 1.69 |
| Dried fiber | 6645 | 2990 | 45% | 2273 | 76% | 3.00 | 5.20 |
|  | 5437 | 2990 | 55% | 2273 | 76% | 2.45 | 6.36 |
|  | 4600 | 2990 | 65% | 2273 | 76% | 1.91 | 7.51 |
|  | 3987 | 2990 | 75% | 2273 | 76% | 1.36 | 8.67 |
|  | 3518 | 2990 | 85% | 2273 | 76% | 0.82 | 9.82 |

| Termo-meso | Ton | DM ton | DM % | VS ton | VS % of TS | NH4+ kg/ton | Norg kg/ton |
|---|---|---|---|---|---|---|---|
| Basis feed stock | 45500 | 5210 | 11.5% | 4485 | 86% | 2.99 | 2.41 |
| Concentrate from sep | 13093 | 1571 | 12.0% | 1178 | 75% | 3.53 | 1.34 |
| N-striped biomass | 15717 | 2804 | 17.8% | 1688 | 60% | 0.60 | 2.02 |
| N-striped concentrate | 0 | 0 | 0.0% | 0 | 0% | 0.00 | 0.00 |
| N-striped conc - pre-dig | 10456 | 1542 | 14.8% | 1151 | 75% | 0.63 | 1.67 |
| Total input | 84766 | 11127 | 13.1% | 8501 | 76% | 2.34 | 2.08 |
| Degasified | 83780 | 7141 | 8.8% | 4515 | 63% | 3.65 | 0.98 |
| Fiber from separation | 8162 | 2857 | 35% | 2142 | 75% | 2.60 | 3.89 |
| Concentrate from sep | 13093 | 1571 | 12.0% | 1178 | 75% | 3.53 | 1.33 |
| P-sediment from sep | 7141 | 1428 | 20.0% | 357 | 25% | 3.21 | 2.78 |
| Permeate | 52384 | 1285 | 2.5% | 838 | 65% | 3.91 | 0.20 |
| Total out | 80780 | 7141 | 8.8% | 4515 | 63% | 3.65 | 0.98 |
| Dried fiber | 6317 | 2843 | 45% | 2132 | 75% | 2.20 | 5.00 |
|  | 5168 | 2843 | 55% | 2132 | 75% | 1.80 | 6.11 |
|  | 4373 | 2843 | 65% | 2132 | 75% | 1.40 | 7.22 |
|  | 3790 | 2843 | 75% | 2132 | 75% | 1.00 | 8.33 |
|  | 3344 | 2843 | 85% | 2132 | 75% | 0.60 | 9.44 |

In Table 6 is a scenario to be considered as minimum share equal to a situation where 70% of the dry matter comes from dried pre-digested or dried termo/meso fibers. Size of production is 18000 ton of mushroom substrate, 3000 ton of mushrooms and 15000 ton of spent substrate, as illustrated in FIG. 9.

TABLE 6

New food linked to Bioenergy Plant
Number of bottles 15 mio
INPUT

|  | DM in % | % of total DM | g pr bottle | value Euro/kg | uro cent pr bottle | Total ton | Total mio Euro | NH4 kg/ton | Norg kg/ton |
|---|---|---|---|---|---|---|---|---|---|
| Dried fiber 1 | 45% | 35% | 309 | 0.10 | 30.0 | 4631 | 0.45 | 3.00 | 5.20 |
| Dried fiber 2 | 45% | 35% | 309 | 0.08 | 26.0 | 4631 | 0.39 | 2.20 | 5.00 |
| Rise bran | 90% | 0% | 0 | 0.22 | 0.0 | 0 | 0.00 | 0.00 | 0.00 |
| Residue from soya | 90% | 3% | 13 | 0.35 | 4.6 | 198 | 0.07 | 0.00 | 0.00 |
| Wheat bran | 90% | 5% | 22 | 0.19 | 4.2 | 331 | 0.06 | 0.30 | 23.00 |
| Oister shells | 90% | 0% | 0 | 0.06 | 0.0 | 0 | 0.00 | 0.00 | 0.00 |
| Sugar beet pulp | 90% | 2% | 9 | 0.32 | 2.8 | 132 | 0.04 | 0.10 | 12.00 |
| Sawdust dried | 90% | 20% | 88 | 0.08 | 7.1 | 1323 | 0 | 0.00 | 0.00 |
| Total | 53% | 100% | 750 | 0.10 | 74.7 | 11246 | 1.12 | 2.15 | 5.02 |
| Drymatter |  |  | 397 |  |  |  |  |  |  |
| Water |  |  | 353 |  |  |  |  |  |  |

TABLE 6-continued

New food linked to Bioenergy Plant
Number of bottles 15 mio
INPUT

|  | DM in % | % of total DM | g pr bottle | value Euro/kg | uro cent pr bottle | Total ton | Total mio Euro | NH4 kg/ton | Norg kg/ton |
|---|---|---|---|---|---|---|---|---|---|
| Added N-water Substrate | 0% |  | 453 | 0.00 | 0.0 | 6795 | 0.00 | 0.10 | 0.00 |
| Total | 33% |  | 1203 |  | 74.7 | 18041 | 1.12 | 1.38 | 3.13 |

In Table 7 is a scenario to be considered as maximum share equal to a situation where 90% of the dry matter comes from dried pre-digested or dried termo/meso fibers.

TABLE 7

Substrate production - Mushroom
Number of bottles 15 mio

| Input | DM in % | % of total DM | g pr bottle | value Euro/kg | uro cent pr bottle | Total ton | Total mio Euro | NH4 kg/ton | Norg kg/ton |
|---|---|---|---|---|---|---|---|---|---|
| Dried fiber 1 | 85% | 45% | 210 | 0.10 | 20.4 | 3152 | 0.31 | 0.82 | 9.82 |
| Dried fiber 2 | 85% | 45% | 210 | 0.08 | 17.7 | 3152 | 0.27 | 0.60 | 9.44 |
| Rise bran | 90% | 0% | 0 | 0.22 | 0.0 | 0 | 0.00 | 0.00 | 0.00 |
| Residue from soya | 90% | 3% | 13 | 0.35 | 4.6 | 198 | 0.07 | 0.00 | 0.00 |
| Wheat bran | 90% | 5% | 22 | 0.19 | 4.2 | 331 | 0.06 | 0.30 | 23.00 |
| Oister shells | 90% | 0% | 0 | 0.06 | 0.0 | 0 | 0.00 | 0.00 | 0.00 |
| Sugar beet pulp | 90% | 2% | 9 | 0.32 | 2.8 | 132 | 0.04 | 0.10 | 12.00 |
| Sawdust dried | 90% | 0% | 0 | 0.08 | 0.0 | 0 | 0.00 | 0.00 | 0.00 |
| Total | 85% | 100% | 464 | 0.11 | 49.7 | 6965 | 0.75 | 0.66 | 10.04 |
| Drymatter |  |  | 397 |  |  |  |  |  |  |
| Water |  |  | 67 |  |  |  |  |  |  |
| Added N-water | 0% |  | 738 | 0.00 | 0.0 | 11076 | 0.00 | 0.10 | 0.00 |
| Total | 33% |  | 1203 |  | 49.7 | 18041 | 0.75 | 0.32 | 3.87 |

Table 8 below contains an illustration of one scenario to be considered as expected share equal to a situation where 80% of the dry matter comes from dried pre-digested fibers with 75% dry matter and dried termo/meso fibers with 65% dry matter.

TABLE 8

Substrate production - Mushroom
Number of bottles 15 mio

| Input | DM in % | % of total DM | g pr bottle | value Euro/kg | uro cent pr bottle | Total ton | Total mio Euro | NH4 kg/ton | Norg kg/ton |
|---|---|---|---|---|---|---|---|---|---|
| Dried fiber 1 | 75% | 40% | 212 | 0.10 | 20.6 | 3175 | 0.31 | 1.36 | 8.67 |
| Dried fiber 2 | 65% | 40% | 244 | 0.08 | 20.6 | 3664 | 0.31 | 1.40 | 7.22 |
| Rise bran | 90% | 0% | 0 | 0.22 | 0.0 | 0 | 0.00 | 0.00 | 0.00 |
| Residue from soya | 90% | 3% | 13 | 0.35 | 4.6 | 198 | 0.07 | 0.00 | 0.00 |
| Wheat bran | 90% | 5% | 22 | 0.19 | 4.2 | 331 | 0.06 | 0.30 | 23.00 |
| Oister shells | 90% | 0% | 0 | 0.06 | 0.0 | 0 | 0.00 | 0.00 | 0.00 |
| Sugar beet pulp | 90% | 2% | 9 | 0.32 | 2.8 | 132 | 0.04 | 0.10 | 12.00 |
| Sawdust dried | 90% | 10% | 44 | 0.08 | 3.5 | 662 | 0.05 | 0.00 | 0.00 |
| Total | 73% | 100% | 544 | 0.10 | 56.3 | 8162 | 0.84 | 1.17 | 7.74 |
| Drymatter |  |  | 397 |  |  |  |  |  |  |
| Water |  |  | 147 |  |  |  |  |  |  |
| Added N-water | 0% |  | 659 | 0.00 | 0.0 | 9879 | 0.00 | 0.10 | 0.00 |
| Total | 33% |  | 1203 |  | 56.3 | 18041 | 0.84 | 0.59 | 3.50 |

The invention claimed is:

1. A method for cultivating fungal cells, said method comprising the steps of:
   a) providing a fermented biomass material comprising solid and liquid parts from a biogas fermenter following an anaerobic fermentation and biogas production,
   b) subjecting the fermented biomass material of step a) to one or more separation steps resulting in the provision of:
      i) a fibrous solid fraction comprising organic and inorganic nitrogen parts and having a reduced content (w/w) of water, and comprising one or more macromolecular nutrient constituents selected from the group consisting of cellulose, hemicellulose, lignin and lignocellulose, and
      ii) at least one liquid fraction comprising solid and liquid organic and inorganic phosphor-containing parts,
   c) subjecting the fibrous solid fraction of step b) to a sanitation treatment comprising the steps of:
      i) heating the fibrous solid fraction of stop b) to a temperature of at least 70° C., wherein said treatment 1) reduces or eliminates viable microorganisms present in the fibrous solid, fraction, and 2) reduces volatile nitrogen-containing compounds and/or precursor volatile compounds present in the fibrous solid fraction, thereby obtaining a fibrous solid fraction comprising organic and inorganic nitrogen parts having a reduced content of volatile nitrogen-containing compounds directly suitable for use as a fibrous solid substrate for cultivating fungal cells;
   d) providing fungal cells and/or spores,
   e) contacting the fungal cells and/or spores with the fibrous solid substrate of step c), and
   f) cultivating the fungal cells and/or spores in said substrate, thereby producing a spent fungal substrate.

2. The method according to claim 1, wherein said sanitation treatment of step c) comprises the steps of:
   heating the fibrous solid fraction to a temperature of 70° C. to 500° C., under alkaline pH conditions, and/or
   subjecting the fibrous solid fraction to a pressure of more than 1 bar.

3. The method according to claim 1, wherein said fibrous solid fraction of step c) is:
   subjected to one or more steps of heating, drying, evaporation, pressure, and/or alkaline pH conditions, and/or
   supplemented with one or more solid and/or liquid supplemental nutrient substrate compositions.

4. The method according to claim 1, further comprising draining liquid parts from the fibrous solid fraction comprising solid and liquid parts and obtaining a fibrous solid fraction comprising organic and inorganic nitrogen parts and having a total dry matter content of more than 25% (w/w), and a residual liquid fraction.

5. The method according to claim 4, wherein the residual liquid fraction from the fibrous solid fraction, and the first liquid permeate fraction, are combined to form a combined liquid fraction comprising solid and liquid parts, and subjecting said combined liquid fraction comprising solid and liquid parts to further separation of solid and liquid parts contained therein, wherein said combined liquid fraction is separated into: a) a second solid, phosphor-containing fraction or sediment, b) a second liquid permeate fraction, and c) a solid fraction concentrate comprising solid and liquid parts.

6. The method according to claim 1, further comprising separating solid and liquid parts of the at least one liquid fraction comprising solid and liquid organic and inorganic phosphor-containing parts by fractionation and/or sedimentation, and obtaining a) a fibrous solid fraction, b) a first solid, phosphor-containing fraction or sediment suitable for being used as a phosphor-containing agricultural fertilizer, and c) a first liquid permeate fraction comprising solid and/or liquid nitrogen- and/or phosphor-containing parts.

7. The method according to claim 6, wherein the first solid, phosphor-containing fraction or sediment and the first liquid permeate fraction is obtained by passing the biomass material comprising solid and liquid parts over a first sieve membrane allowing the first solid, phosphor-containing fraction, or sediment, and the first liquid permeate fraction to pass through the membrane, while the fibrous solid fraction is retained and separated from the first solid, phosphor-containing fraction or sediment and the first liquid permeate fraction.

8. The method according to claim 1, wherein the fungal cells and/or spores are selected from the group consisting of: *Basidiomycetes*, Agaricomycetidae, Exohasidioniycetidae, Tremellomycetidae, Ustilaginomycetidae, Agaricus, Lentinula (Lentinus), Flammulina, Pleurotus, Lentinula edodes (shiitake); edible Agaricus species, Agaricus bisporus, Agaricus campestris, Agaricus subrufescens; Flammulina velutipes (Enokitake), Pleurotus eryngii (Eryngii), Pleurotus ostreatus; Shimeji, Lyophyllum shimejl, Buna-shimeji, Bunapi-shimeji, Hatake-chimeji, shirotarnogidake, velvet pioppino; and a fungus capable of digesting cellulose, hemicellulose, lignin and lignocellulose.

9. The method according to claim 1, wherein said fermented biomass material comprising solid and liquid parts from a biogas fermenter is selected from the group consisting of 1) a biomass material comprising solid and liquid nitrogen- and phosphor-containing parts, 2) a spent fungal substrate biomass material and 3) a degassed or partly degassed fermented biomass material.

10. The method according to claim 1, further comprising one or more steps of:
    collecting the spent fungal substrate, wherein said spent fungal substrate is at least partially digested by the cultivation of the fungal cells and is suitable as a feed stock for an anaerobic fermentation and biogas production,
    fermenting the spent fungal substrate under anaerobic fermentation conditions, and/or
    producing a biogas and a degassed spent fungal substrate biomass material comprising organic and inorganic nitrogen parts.

11. The method according to claim 1, wherein said method further comprises the steps of:
    cycling, more than once, spent fungal substrate biomass material from a fungal cultivation, and reusing said substrate biomass material in, an anaerobic biogas fermentation taking place in an anaerobic biogas fermenter, said fermentation resulting in the production of biogas and a degassed fermented biomass material suitable for use as a substrate for cultivating fungal cells and/or spores, and/or
    cycling, more than once, a fibrous solid fraction of a degassed fermented biomass material from said anaerobic biogas fermenter to a fungal cultivation facility, and reusing said degassed fibrous solid fraction from said anaerobic biogas fermenter to cultivate said fungal cells and/or spores
    said fungal cultivation resulting in the provision of fungal cells and/or spores and a spent fungal substrate biomass material suitable for use as a feed stock biomass material in an anaerobic biogas fermentation, and fractionating the degassed fermented biomass material by subjecting the degassed fermented biomass material to one or more separation steps, thereby obtaining a) a fibrous solid fraction comprising solid and liquid parts, and organic and inorganic nitrogen parts, and b) at least one liquid fraction comprising solid and liquid parts.

12. The method of claim 11, further comprising supplementing the anaerobic biogas fermenter by addition of further anaerobically fermentable organic waste biomass material.

13. The method according to claim 1, further comprising the step of controlling the nutrient composition and/or the moisture content of the fibrous solid substrate by converting said one or more supplemental nutrient substrate compositions into one or more volatile compounds and evaporating said one or more volatile compounds from said fibrous solid fraction.

14. The method according to claim 1, wherein said method comprises the further steps of:

subjecting the fermented biomass material to one or more separation steps and obtaining a fibrous solid fraction comprising solid and liquid organic and inorganic nitrogen-comaining parts, and at least one liquid fraction comprising solid and liquid organic and inorganic phosphor-containing parts, separating solid and liquid parts of the at least one liquid fraction by fractionation and/or sedimentation, and obtaining a) a fibrous solid fraction comprising solid and liquid parts comprising organic and inorganic nitrogen parts, b) a first solid, phosphor- containing fraction or sediment suitable for use as a phosphor-containing agricultural fertilizer, and c) a first liquid permeate fraction comprising solid and/or liquid nitrogen- and/or phosphor-containing parts.

15. The method according to claim 1, wherein prior to providing a fermented biomass material following an anaerobic fermentation and biogas production according to step a), said method further comprises the steps of:

performing a first anaerobic fermentation of a first fermentable biomass material in one or more pre-fermentation facility or first fermentation facility unit(s), thereby obtaining a first fermented biomass material, and producing and collecting first volatile nitrogen-containing compounds, separating at least partly the first fermented biomass material from the first volatile nitrogen-containing compounds and obtaining a separated, first fermented biomass having a reduced content of first volatile nitrogen-containing compounds, and/or a reduced content of carbon and nitrogen containing precursor compounds capable of being converted into first volatile carbon and, nitrogen-containing compounds during a fermentation, diverting the separated, first fermented biomass to a second fermentation facility for producing second volatile methane-containing compounds, and performing a second anaerobic fermentation of the separated, first fermented biomass, in the second fermentation facility, thereby obtaining a second fermented biomass material, and producing and collecting at least second volatile methane-containing compounds.

16. The method of claim 15, wherein the first fermented biomass is supplemented with additional organic waste biomass material.

17. The method according to claim 1, wherein said volatile nitrogen-containing, compounds are selected from the group consisting of gaseous ammonia, ammonia, inorganic nitrogen; an aqueous gas comprising ammonia; an aqueous gas comprising ammonia and volatile sulphur-containing compounds; and wherein said precursor volatile compounds are selected from ammonium and ammonium salts.

18. The method according to claim 1, wherein said volatile nitrogen-containing compounds and/or precursor volatile compounds are diverted to and/or collected in a stripper and sanitation tank.

19. The method according to claim 1, wherein said volatile nitrogen-containing compounds comprise gaseous ammonia which ammonia gas is converted to a solid ammonium salt compound by reaction with an acid.

20. The method according to claim 1, wherein said sanitation treatment exploits primary and secondary combustion air sources, including exhaust air sources, present in or generated in the biogas fermentation facility as a result of performing said sanitation, wherein said primary and secondary combustion air sources are diverted to a stripper and sanitation tank for conversion and/or collection as solids.

21. The method according to claim 20, wherein the exploitation of primary combustion air sources from the biogas fermentation facility results in generating a negative pressure in the biogas fermentation facility space, said negative pressure prevention or contributing to preventing any undesirable odorants from escaping the biogas fermentation facility, wherein said odorants comprise one or more volatile nitrogen-containing compounds and/or volatile sulphur-containing compounds.

22. The method according to claim 1, wherein said fermented biomass material is selected from the group consisting of biomasses comprising manures and slurries thereof, biomasses comprising crop residues, biomasses comprising silage crops, biomasses comprising animal carcasses and fractions thereof, slaughterhouse waste products, dairy waste products, meat and bone meal, animal category 2 waste products; one or more complex biomasses; a complex biomass comprising protein, oily substances and fats; a complex biomass selected from the group consisting of organic municipal waste, foodstuff waste, fermentable organic industrial waste products, fish waste products, slaughterhouse waste; deep litter or manure from animals, especially from cattle, pigs and poultry holdings; animal carcasses and/or fractions thereof, meat and bone meal, blood plasma and any produce originating from animals, straw, fibers and sawdust.

* * * * *